US011650094B2

(12) United States Patent
Borkholder et al.

(10) Patent No.: US 11,650,094 B2
(45) Date of Patent: May 16, 2023

(54) SYSTEMS, DEVICES, AND METHODS FOR MEASURING LOADS AND FORCES OF A SEATED SUBJECT USING SCALE DEVICES

(71) Applicant: Casana Care, Inc., Rochester, NY (US)

(72) Inventors: David A. Borkholder, Canandaigua, NY (US); Austin McChord, Norwalk, CT (US); Nicholas Joseph Conn, Fairport, NY (US); Steve Petrucelli, Cranbury, NJ (US)

(73) Assignee: Casana Care, Inc., Rochester, NY (US)

( * ) Notice: Subject to any disclaimer, the term of this patent is extended or adjusted under 35 U.S.C. 154(b) by 0 days.

(21) Appl. No.: 17/845,883

(22) Filed: Jun. 21, 2022

(65) Prior Publication Data

US 2022/0364904 A1 Nov. 17, 2022

Related U.S. Application Data

(63) Continuation of application No. PCT/US2022/028787, filed on May 11, 2022.
(Continued)

(51) Int. Cl.
*G01G 19/44* (2006.01)
*G01G 19/52* (2006.01)
(Continued)

(52) U.S. Cl.
CPC ............. *G01G 19/44* (2013.01); *A61B 5/053* (2013.01); *A61B 5/6887* (2013.01); *G01G 19/52* (2013.01);
(Continued)

(58) Field of Classification Search
CPC ........ G01G 19/44; G01G 19/50; G01G 19/52; G01G 21/22; G01G 21/28; G01G 23/012; A61B 5/053; A61B 5/6887
See application file for complete search history.

(56) References Cited

U.S. PATENT DOCUMENTS

| 4,203,497 | A | * | 5/1980 | Harris | .................. | G01G 19/025 177/244 |
| 4,212,361 | A | * | 7/1980 | Stocker | .................. | G01G 23/10 177/21 OEM |

(Continued)

FOREIGN PATENT DOCUMENTS

| CA | 1324415 C | 11/1993 |
| CN | 100502773 C | 6/2009 |

(Continued)

OTHER PUBLICATIONS

Non-Final Office Action dated Jan. 26, 2017 for U.S. Appl. No. 15/190,534, 6 pages.
(Continued)

*Primary Examiner* — Randy W Gibson
(74) *Attorney, Agent, or Firm* — Cooley LLP

(57) ABSTRACT

Systems, devices, and methods are disclosed herein for monitoring physiological data of subjects seated on a toilet, including systems, devices, and methods for monitoring loads and forces on a scale device. In some embodiments, systems, devices, and methods disclosed herein include a set of sensors that can measure loads and forces present at a scale device receiving the feet of an individual seated in a toilet.

32 Claims, 15 Drawing Sheets

Related U.S. Application Data

(60) Provisional application No. 63/187,036, filed on May 11, 2021.

(51) Int. Cl.

| | |
|---|---|
| *G01G 21/22* | (2006.01) |
| *G01G 21/28* | (2006.01) |
| *G01G 23/01* | (2006.01) |
| *A61B 5/05* | (2021.01) |
| *A61B 5/053* | (2021.01) |
| *A61B 5/00* | (2006.01) |

(52) U.S. Cl.
CPC .............. *G01G 21/22* (2013.01); *G01G 21/28* (2013.01); *G01G 23/012* (2013.01)

(56) References Cited

U.S. PATENT DOCUMENTS

| | | | |
|---|---|---|---|
| 4,697,656 A | 10/1987 | de Canecaude | |
| 4,711,313 A * | 12/1987 | Iida | G01G 21/28 177/127 |
| 4,969,112 A * | 11/1990 | Castle | G01G 23/3728 340/505 |
| 6,727,438 B1 | 4/2004 | Stokes | |
| 7,437,781 B2 | 10/2008 | Rigas | |
| 7,521,638 B1 * | 4/2009 | Godshaw | G01G 21/28 177/126 |
| 8,827,918 B2 | 9/2014 | Kim et al. | |
| 8,983,854 B2 | 3/2015 | Park et al. | |
| 9,595,185 B1 * | 3/2017 | Hall | G01G 19/50 |
| 9,829,311 B1 | 11/2017 | Wilson et al. | |
| 10,292,658 B2 | 5/2019 | Borkholder et al. | |
| 11,234,651 B2 | 2/2022 | Borkholder et al. | |
| 2002/0188205 A1 | 12/2002 | Mills | |
| 2003/0233034 A1 | 12/2003 | Varri et al. | |
| 2004/0112149 A1* | 6/2004 | Gebert | G01G 7/06 177/133 |
| 2005/0228305 A1 | 10/2005 | Nagata et al. | |
| 2006/0111641 A1 | 5/2006 | Manera et al. | |
| 2006/0258915 A1 | 11/2006 | Ueda et al. | |
| 2008/0194975 A1 | 8/2008 | MacQuarrie et al. | |
| 2010/0094147 A1 | 4/2010 | Inan et al. | |
| 2013/0310700 A1 | 11/2013 | Wiard et al. | |
| 2014/0039330 A1 | 2/2014 | Seo et al. | |
| 2014/0142396 A1 | 5/2014 | Ricks et al. | |
| 2014/0142437 A1 | 5/2014 | Inan et al. | |
| 2014/0142451 A1 | 5/2014 | Kim et al. | |
| 2016/0317043 A1 | 11/2016 | Campo et al. | |
| 2016/0374618 A1 | 12/2016 | Giovangrandi | |
| 2016/0374619 A1 | 12/2016 | Borkholder et al. | |
| 2018/0020984 A1 | 1/2018 | Hall et al. | |
| 2018/0042386 A1* | 2/2018 | Hall | H04R 1/028 |
| 2018/0084960 A1 | 3/2018 | Iwabata et al. | |
| 2019/0008457 A1 | 1/2019 | Hall et al. | |
| 2019/0178704 A1* | 6/2019 | Lui | G01G 19/50 |
| 2019/0231271 A1 | 8/2019 | Borkholder et al. | |
| 2019/0298316 A1 | 10/2019 | Kashyap et al. | |
| 2020/0289000 A1 | 9/2020 | Hall et al. | |
| 2020/0390367 A1 | 12/2020 | Hall et al. | |
| 2020/0390422 A1 | 12/2020 | Hall et al. | |
| 2022/0218286 A1 | 7/2022 | Borkholder et al. | |

FOREIGN PATENT DOCUMENTS

| | | |
|---|---|---|
| CN | 102660988 B | 9/2012 |
| CN | 203042108 U | 7/2013 |
| CN | 210 123 304 U | 3/2020 |
| DE | 10 2010 061 035 A1 | 6/2012 |
| EP | 1 488 739 A1 | 12/2004 |
| JP | H04-367638 A | 12/1992 |
| JP | 2000-254040 A1 | 9/2000 |
| JP | 2010172498 A | 8/2010 |
| JP | 2020-153896 A | 9/2020 |
| KR | 2017/0125696 A | 11/2017 |
| WO | WO 2005/070288 A1 | 8/2005 |
| WO | WO 2021/055681 A1 | 3/2021 |

OTHER PUBLICATIONS

Final Office Action dated Oct. 6, 2017 for U.S. Appl. No. 15/190,534, 6 pages.

Non-Final Office Action dated Feb. 22, 2018 for U.S. Appl. No. 15/190,534, 9 pages.

Final Office Action dated Sep. 4, 2018 for U.S. Appl. No. 15/190,534, 9 pages.

Advisory Action dated Nov. 13, 2018 for U.S. Appl. No. 15/190,534, 4 pages.

Non-Final Office Action dated Jul. 6, 2020 for U.S. Appl. No. 16/377,938, 10 pages.

Non-Final Office Action dated Dec. 1, 2020 for U.S. Appl. No. 16/377,938, 9 pages.

Invitation to Pay Additional Fees dated Jul. 20, 2022 for International Application No. PCT/US2022/024236, 21 pages.

International Search Report and Written Opinion dated Aug. 5, 2022 for International Application No. PCT/US2022/028787, 23 pages.

Arias, D. E et al., "Data collection capabilities of a new non-invasive monitoring system for patients with advanced multiple sclerosis," AMIA Annual Symposium Proceedings, 2013:61-68 (2013).

Baek, H. J. et al., "System for Unconstrained ECG Measurement on a Toilet Seat using Capacitive Coupled Electrodes: The Efficacy and Practicality," Annu Int Conf IEEE Eng Med Biol Soc., Aug. 20-24, 2008; pp. 2326-2328, Vancouver, British Columbia, Canada.

Chen, Z. et al., "Noninvasive Monitoring of Blood Pressure Using Optical Ballistocardiography and Photoplethysmograph Approaches," 35th Annual International Conference of the IEEE EMBS, Jul. 3-7, 2013, pp. 2425-2428, Osaka, Japan.

Huang, J. -J. et al., "Development of the smart toilet equipment with measurements of physiological parameters," 2012 9th International Conference on Ubiquitous Intelligence and Computer and 9th International Conference on Autonomic and Trusted Computing, 2012, pp. 9-16; doi: 10.1109/UIC-ATC.2012.143.

Inan, O. T. et al., "Robust ballistocardiogram acquisition for home monitoring," Physiol Meas, 30(2):169-85 (2009); doi: 10.1088/0967-3334/30/2/005.

Javaid, A. Q. et al., "Quantifying and Reducing Posture-Dependent Distortion in Ballistocardiogram Measurements," IEEE Journal of Biomedical and Health Informatics, 19(5):1549-1556 (2015).

Junnila, S. et al., "An EMFi-film sensor based ballistocardiographic chair: performance and cycle extraction method," IEEE Workshop on Signal Processing Systems Design and Implementation, 2005, pp. 373-377.

Kim, J. S. et al., "Multi-channel measurement of photo-plethysmography and evaluation for the optimal site of a thigh in a toilet," 26th Annual International Conference of the IEEE, Sep. 1-5, 2004, pp. 3366-3368, San Francisco, California, USA.

Kim, K. K. et al., "The electrically noncontacting ECG measurement on the toilet seat using the capacitively-coupled insulated electrodes," The 26th Annual International Conference of the IEEE Engineering in Medicine and Biology Society, San Francisco, CA, USA, 2004, pp. 2375-2378, doi:10.1109/IEMBS.2004.1403688.

Kim, J. S. et al., "A new approach for non-intrusive monitoring of blood pressure on a toilet seat," Physiological Measurement, 27:203-211 (2006).

Lim, Y.G. et al., "Capacitive Measurement of ECG for Ubiquitous Healthcare," Annals of Biomedical Engineering, 42(11):2218-2227 (2014).

Motoi, K. et al., "Development and Clinical Evaluation of a Home Healthcare System Measuring in Toilet, Bathtub and Bed without Attachment of Any Biological Sensors," Proceedings of the 10th IEEE International Conference on Information Technology and Applications in Biomedicine, Corfu, Greece, 2010, pp. 1-4, doi: 10.1109/ITAB.2010.5687774.

Motoi, K. et al., "Development of a fully automated network system for long-term health-care monitoring at home," Proceedings of the

(56) References Cited

OTHER PUBLICATIONS

29th Annual International Conference of the IEEE EMBS, Aug. 23-26, 2007, pp. 1826-1829, Cite Internationale, Lyon, France.

Park, K. S., "Nonintrusive Measurement of Biological Signals for Ubiquitous Healthcare," 31st Annual International Conference of the IEEE EMBS, Sep. 2-6, 2009, pp. 6573-6575, Minneapolis, Minnesota, USA.

Prisk, G. K. et al., "Three-dimensional ballistocardiography and respiratory motion in sustained microgravity," Aviation Space and Environmental Medicine, 72(12):1067-1074 (2002).

Schlebusch, T., "Unobtrusive Health Screening on an Intelligent Toilet Seat," ACTA Polytechnica, 51(5):94-99 (2011); http://www.tk.de/tk/innovative-verfahren/telemedizin/herz/9784.

Shin, J. H. et al., "Ubiquitous House and Unconstrained Monitoring Devices for Home Healthcare System," 2007 6th International Special Topic Conference on Information Technology Applications in Biomedicine, Tokyo, Japan, 2007, pp. 201-204, doi: 10.1109/ITAB.2007.4407381.

Tanaka, S. et al., "Fully Automatic System for Monitoring Blood Pressure from a Toilet Seat Using Volume-Oscillometric Method," Proceedings of the 2005 IEEE Engineering in Medicine and Biology, 27th Annual Conference, Sep. 1-4, 2005, pp. 3939-3941, Shanghai, China.

Tavakolian, K. et al., "Comparative analysis of infrasonic cardiac signals," Computers in Cardiology, 36:757-760 (2009).

Togawa, T. et al., "Physiological Monitoring Systems Attached to the Bed and Sanitary Equipment," Images of the Twenty-First Century. Proceedings of the Annual International Engineering in Medicine and Biology Society, Seattle, WA, USA, 1989, pp. 1461-1463 vol. 5, doi: 10.1109/IEMBS.1989.96289.

Weber, T. et al., "Noninvasive determination of carotid-femoral pulse wave velocity depends critically on assessment of travel distance: a comparison with invasive measurement," Journal of Hypertension, 27(8):1624-1630 (2009).

Yamakoshi, K. et al., "Non-conscious and Automatic Acquisition of body and Excreta Weight Together with Ballistocardiogram in a Lavatory," 18th Annual International Conference of the IEEE Engineering in Medicine and Biology Society, 1996, pp. 67-68, Amsterdam, 1.1.6:Home Health Monitoring.

International Search Report and Written Opinion dated Sep. 12, 2022 for International Application No. PCT/US2022/024236, 24 pages.

Invitation to Pay Additional Fees dated Sep. 9, 2022 for International Application No. PCT/US2022/029646, 15 pages.

\* cited by examiner

SYSTEMS, DEVICES, AND METHODS FOR MEASURING LOADS AND FORCES OF A SEATED SUBJECT USING SCALE DEVICES

CROSS-REFERENCE TO RELATED APPLICATIONS

This application is a continuation of International Patent Application No. PCT/US2022/028787, entitled "Systems, Devices, and Methods for Measuring Loads and Forces of a Seated Subject Using Scale Devices," filed May 11, 2022, which claims the benefit of U.S. Provisional Patent Application Ser. No. 63/187,036, entitled "Systems, Devices, and Methods for Measuring Loads and Forces of a Seated Subject Using Scale Devices," filed May 11, 2021, the disclosures of which are incorporated by reference herein in their entireties.

TECHNICAL FIELD

The embodiments described herein relate generally to health monitoring systems, and more particularly to systems and methods for monitoring physiological characteristics of subjects seated on a toilet, including systems and methods for measuring loads and forces of a seated subject using scale devices.

BACKGROUND

Patient health monitoring is an important tool in tracking physiological conditions of patients and to provide early warnings or guidance to individuals and healthcare providers in cases of patient health deterioration. Oftentimes, patient monitoring is obtrusive and requires individuals to actively wear certain devices or change their routine to be able to measure certain vital signs or characteristics of the patient. Unobtrusive systems for monitoring individuals are also limited and can provide inaccurate results. Therefore, there exists a need to develop more accurate approaches to monitoring individuals through unobtrusive means.

SUMMARY

Systems, devices, and methods are described herein for measuring data (e.g., loads or forces) of individuals seated on a toilet using scale devices.

In some embodiments, an apparatus includes: a scale disposable on a surface in front of a toilet, the scale including: a panel configured to receive a foot of a subject seated on the toilet; and a plurality of sensors disposed below the panel and distributed about a perimeter of the panel, the set of sensors collectively configured to measure forces present on the panel when the foot is received on the panel; and a surround structure disposed around the scale and configured to prevent movement of one or more components of the scale during use, the scale and the surround structure defining a convex shape configured to fit against a base of the toilet such that the subject seated on the toilet can place the foot on the panel.

In some embodiments, a system includes: a first set of sensors disposed about a ring of a toilet, the first set of sensors collectively configured to measure forces present on the ring when a subject is seated on the ring; and a scale assembly disposable adjacent to the toilet, the scale assembly including: a set of one or more panels configured to receive the feet of the subject when the subject is seated on the ring; and a second set of sensors disposed beneath and distributed about the set of panels, the second set of sensors collectively configured measure forces present on the set of panels when the feet are received on the set of panels; and a processor operatively coupled to the first and second sets of sensors and configured to receive signals indicative of the forces measured by the first and second sets of sensors, the processor configured to determine at least one of a weight, a ballistocardiogram (BCG), or a posture of the subject based on the signals.

In some embodiments, a method includes: measuring, via a first set of sensors disposed about a ring of a toilet, forces present on the ring when a subject is seated on the ring; measuring, via a second set of sensors disposed in a scale assembly, forces present on the scale assembly when the subject seated on the ring places his feet on the scale assembly; and determining, based on the forces measured by the first and second sets of sensors, at least one of a weight, a ballistocardiogram (BCG), or a posture of the subject.

DETAILED DESCRIPTION

Figure 1:
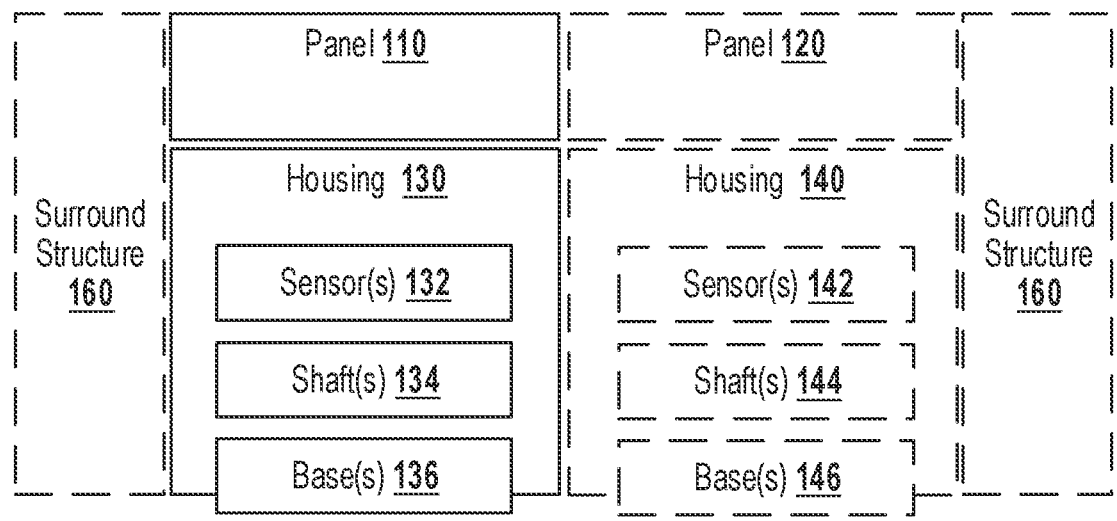
FIG. 1 is a schematic illustration of a scale device for measuring data (e.g., loads or forces) associated with a subject seated on a toilet, according to an embodiment.

The embodiments described herein relate to generally to health monitoring systems, and more particularly to systems and methods for measuring data such as loads or forces associated with an individual seated on a toilet using a scale device. In some embodiments, a scale device can be used with one or more sensors on a toilet seat to measure a weight, ballistocardiogram (BCG), or posture of an individual seated on the toilet, which can be used to monitor certain physiological data or conditions of the individual and to inform the individual and/or healthcare providers of changes in such data or conditions necessitating certain therapies, treatments, lifestyle changes, etc.

Most individuals use toilets on a daily basis. Accordingly, health monitoring that can be conducted while an individual is seated on a toilet can provide an unobtrusive way of regularly monitoring information about the individual. Measures such as a weight or BCG of an individual seated on a toilet can be useful for monitoring certain conditions of the individual, such as, for example, a cardiac or vascular heath of the individual.

Monitoring of certain physiological data of individuals seated on toilets, however, can be difficult, e.g., when an individual's weight may be distributed across a toilet seat and the floor. For example, sensors placed where an individual is seated (e.g., along a toilet seat or ring) can monitor weight associated with the individual but these may be incomplete. The individual is likely to place their feet along the floor in front of the toilet, and certain weight of the individual transferred through the individual's feet directly to the ground would not be captured by the sensors on the toilet seat. Accordingly, systems and methods described herein provide a scale device that can be placed in front of a toilet to measure loads or forces associated with an individual seated on the toilet. In some embodiments, the scale device can be used to measure a partial weight of an individual, e.g., via the forces exerted by the individual's feet on the scale device. In some embodiments, the scale device in combination with sensors positioned where the user is seated (e.g., along a toilet seat or ring) can be used to obtain a more complete measurement of a weight of an individual, e.g., via the forces exerted by the individual's feet on the scale device and the forces exerted by the individual's bottom and/or legs on the toilet seat.

Weight can be used to monitor and assess a number of conditions associated with an individual, including for example body weight of a seated individual, a weight change due to defecation or urination, level of fluid retention, etc. Such conditions can be indicative of certain types of diseases including for example, heart failure and kidney failure. Dynamic forces on a scale device can also be indicative of characteristics associated with an individual's respiration, BCG, urination, defection, etc. In many instances, the magnitude of dynamic forces generated by an individual seated on a toilet and exerted on a scale device are small but important to accurately determine for various applications, including, for example, estimating pulse wave velocity (PWV), stroke volume, cardiac output, weight of urination, weight of defection, respiration rate, etc.

Various sensing or monitoring systems can be used to measure loads or forces on a toilet. In an embodiment, a floating hinge (e.g., a hinge that bears no loads) can be used in combination with a toilet ring that has four bumpers or supports, which include sensors to measure loads or forces on the ring. Suitable examples of floating hinges are described in U.S. Pat. No. 10,292,658, titled, "Apparatus, System, And Method For Mechanical Analysis Of Seated Individual," issued May 21, 2019 ("the '658 patent"), which is incorporated herein by reference. In an embodiment, a load bearing hinges can be used in combination with a toilet ring comprising bumpers or supports, and a number of sensors disposed about the toilet ring and at the hinge to account for loads present on the toilet ring and the hinge. In an embodiment, a seat and/or toilet attachment can be coupled to a ring or bowl of a toilet and sensors can be disposed about the seat and/or toilet attachment to measure loads present on the ring or bowl. Suitable examples of devices with sensors disposed about hinges and seat and/or toilet attachments are described in International Patent Application Number PCT/US2022/024236 entitled, "Systems, Devices, and Methods for Monitoring Loads and Forces on a Seat," filed Apr. 11, 2022 ("the '236 application"), which is incorporated herein by reference.

Systems, devices, and methods described herein provide a scale device that can measure loads exerted by an individual through their feet when seated at a toilet or standing on the scale device. Existing scale devices may not be designed for placement in front of a toilet or be suitable for measuring a partial weight of an individual when the individual is seated at the toilet. Scale devices described herein address these limitations.

FIG. 1 is a schematic illustration of a sensing system implemented as a scale assembly 100, according to some embodiments. The scale assembly or scale device 100 can be configured to measure forces or loads present on a surface of one or more panel(s) 110, 120 of one or more scales when a subject (e.g., an individual) is seated at a toilet and has placed his feet on top of the one or more panel(s) 110, 120 and/or when the subject is standing on the scale assembly 100. In some embodiments, the scale assembly 100 can include multiple scales, such as a first scale with a panel 110 for receiving a subject's left foot and a second scale with a panel 120 for receiving the subject's right foot. In other embodiments, the scale assembly 100 can include a single scale with a panel 110, which can receive a subject's left and right feet. In some embodiments, each scale can be configured to operate independently and can include components that are structurally and/or functionally similar to the other scale. In some embodiments, the two scales can be configured to operate collectively to provide data about a subject. For example, the two scales can be configured to share one or more components, e.g., a processor and/or power source, and/or data collected by the sensor(s) 132, 142 of the two scales can be synchronized.

The panel 110 can be positioned above a housing 130, sensor(s) 132, shaft(s) 134, and base(s) 136. Optionally, if there is a second scale, the panel 120 can be positioned above a housing 140, sensor(s) 142, shaft(s) 144, and base(s) 146. The panel 120, housing 140, sensor(s) 142, shaft(s) 144, and base(s) 146 can be structurally and/or functionally similar to the panel 110, housing 130, sensor(s) 132, shaft(s) 134, and base(s) 136, respectively. Accordingly, the descriptions provided below of the panel 110, housing 130, sensor(s) 132, shaft(s) 134, and base(s) 136 are also applicable to the panel 120, housing 140, sensor(s) 142, shaft(s) 144, and base(s) 146, respectively.

In some embodiments, the scale assembly 100 can be used in conjunction with a sensing system associated with a toilet seat, e.g., such as any of the sensing devices or systems described in the '236 application. Further details of such are provided with reference to FIG. 2.

The panel 110 can be configured to receive one or both feet of a user. In some embodiments, the panel 110 can be configured to receive a single foot of a subject (e.g., a left foot or right foot), while in other embodiments, the panel 110 can be configured to receive both feet of a subject. The panel 110 can be designed such that a subject can be seated on a toilet can rest one or both feet on the panel 110. The panel 110 can have a top surface having any suitable shape for receiving a foot or feet of the subject, e.g., a rectangular shape, a square shape, a circular shape, an oval shape, an elliptical shape, or any other shape that is sufficiently large to receive the foot or feet of the subject. The panel 110 can be positioned on or over other components of the scale assembly 100, e.g., such that the panel 110 defines a continuous solid surface suitable to support the foot or feet of the subject seated on the toilet. In some embodiments, the panel 110 can be a glass plate or have a glass-top surface. In some embodiments, the panel 110 can be formed of a rigid material other than glass, e.g., a plastic, metal, wood and/or a combination thereof. In some embodiments, the panel 110 can include surface finishes or a top surface configured to provide comfort to a user, provide friction and/or support (e.g., to enhance grip).

The panel 110 can be disposed over a housing 130 that houses one or more internal components of a scale, e.g., sensor(s) 132, shaft(s) 134, electronics, power source, processor, etc. The panel 110 can optionally be bounded by a surround structure 160. Further details of the housing 130 and the surround structure 160 are provided below.

The housing 130 can define one or more areas for accommodating (e.g., housing, containing, supporting, etc.) one or more components of the scale assembly 130. As shown in FIG. 1, the housing 130 can accommodate one or more sensor(s) 132, shaft(s) 134, and base(s) 136 of the scale assembly 100. In some embodiments, the housing 130 can include one or more compartments that can contain, house, and/or accommodate one or more auxiliary component(s), such as, for example, batteries, power sources, lights, data communication ports, processors, and/or input/output devices (e.g., a display or audio device). The housing 130 can be disposed under the panel 110, such that the loads or forces exerted by the foot or feet of a subject seated on a toilet can be sensed and/or registered by sensor(s) 132 disposed within the housing 110, as further described herein. The housing 110 can be formed of any suitable material, including, for example, a metal, plastic, glass, ceramic, and/or combination thereof.

The housing 130 can be shaped to extend along or around a portion of the panel 110. In some embodiments, the housing 130 can have a shape that is substantially similar to or corresponds to the shape and/or dimensions of the panel 110. In other embodiments, the housing 130 can have a smaller footprint than the panel 110, e.g., extend around a portion of a perimeter of the panel 110. In some embodiments, if the panel 110 has a rectangular shape, the housing 130 can have a bracketed or C-shape, with dimensions similar to or smaller than those of the panel 110, as further depicted in and described with reference to FIG. 5. The housing 130 can include a flat surface on top for receiving and supporting the panel 110.

In some embodiments, the housing 130 can be a single component after construction. For example, one or more components of the scale assembly 100 can be placed within a housing section during manufacture, and the housing section can be sealed with other housing sections to form the housing 130. In other embodiments, the housing 130 can include multiple components, sections, portions, and/or covers that can be coupled to and decoupled from one another. For example, the housing 130 can include a first cover (e.g., a first portion) and a second cover (e.g., a second portion). The first and second covers can be coupled together to form the housing, e.g., using fasteners, magnets, clamps, etc.

In some embodiments, the housing 130 can include openings that allow one or more components of a scale to extend out of the housing. For example, the housing 130 can include openings along the bottom that allow one or more base(s) 136 to extend out through the housing 130 and contact a surface that the scale assembly 130 is supported on (e.g., a floor or platform in front of a toilet). The housing 130 can be configured to protect the sensor(s) 132, shaft(s) 134, base(s) 136, and/or other internal components of a scale from external debris and/or other elements. In some embodiments, the housing 130 can be designed to form a water-tight or sealed enclosure around the sensor(s) 132, shaft(s) 134, base(s) 136, and/or other internal components of a scale.

The one or more sensor(s) 132 disposed in the housing 130 can be used to measure one or more signals present on the panel 110. For example, the sensor(s) 132 can be configured to measure parameters that provide information regarding a weight or BCG of a subject seated at a toilet, e.g., by measuring loads or forces present on the panel 110 due to a weight exerted by the subject's feet on the panel. The sensor(s) 132 can be configured to measure changes in the parameters such as changes in loads and/or forces, which can be used to calculate, for example, a weight change due to defecation or urination. In some embodiments, information collected by the sensor(s) 132 can be used to determine the forces generated by a heart of the seated individual. In particular, as the heart forcefully ejects fluid into the aorta of the individual, the body of the individual undergoes a downward and upward force in a repeating pattern, which can cause changes in forces and/or loads exerted by the individual on the panel 110. The sensor(s) 132 can be configured to measure these changes and to provide BCG data for the individual over time. The sensor(s) 132 can be coupled to a processor (e.g., an onboard processor, a complementary sensing system, and/or a processor of a separate compute device (see FIG. 2)) that can use the information collected by the sensor(s) 132 to evaluate various physiological data or conditions of the individual. For example, the forces measured by one or more sensor(s) 132 can be used to estimate information for the medical analysis of cardiac and vascular function of a seated individual, such as, for example, stroke volume, cardiac output, weight and/or speed of urination, weight and/or speed of defecation, respiration rate, and more.

In some embodiments, the data collected by the sensor(s) 132 (e.g., BCG data) can be combined with data produced by other sensors such as, for example a photoplethysmography (PPG) sensor, an electrocardiogram (ECG) sensor and/or one or more force sensors (e.g., included in a complementary sensing system 270). For example, the data collected by sensor(s) 132 in the scale assembly 100 can be combined with data collected by one or more force sensor(s) disposed along a toilet seat (e.g., a toilet ring) to provide a more complete measurement of a weight of a subject seated at a toilet. The sensors disposed along the toilet seat can capture forces exerted by the subject onto the seat, and the sensors disposed in the scale assembly 100 (e.g., sensor(s) 132, 142) can capture forces exerted by the subject onto the scale. The combined data from the seat sensors and the scale sensors can provide a measure that is more representative of a full weight of the subject. In some embodiments, the combined data from the seat sensors and the scale sensors can be used to determine a posture of the individual seated on the toilet, e.g., by assessing a distribution of weight between the sale sensors and seat sensors. In some embodiments, the combined data can be used to estimate relevant information for the medical analysis of cardiac and vascular function. Suitable examples of sensors in toilet seats are described in the '658 patent and the '236 application, incorporated above by reference. Suitable examples of processing and/or evaluation of sensor data are described in the '658 patent, as incorporated by reference above.

Examples of sensor(s) 132 include load and/or force sensors such as load cells (e.g., pneumatic load cells, hydraulic load cells, piezoelectric crystal load cells, inductive load cells, capacitive load cells, magnetostrictive load cells, strain gauge load cells, etc.), strain gages, force sensing resistors (FSR) or printed or flexible force sensors, optical force sensors, etc. With the information from the sensor(s) 132 (and from sensor(s) 142 if a second scale is used), alone or in combination with information generated by a complementary sensing system (as described in further detail with reference to FIG. 2), a processor (e.g., onboard processor of the scale assembly 130 and/or a separate processor (see FIG. 2)) can be used to determine one or more of the following information about an individual or subject: heart rate, heart rate variability, left ventricular ejection time, pre-ejection period, flow velocity, pulse transit time (e.g., based on ECG or BCG data), blood pressure, cardiac output, cardiac contractility, abnormal heart function, blood oxygenation levels (e.g., $SpO_2$), respiration rate, stress levels (e.g., via heart rate variability), body weight, cardiac waveform characteristics (e.g., magnitudes and/or intervals), etc.

The sensor(s) 132 can be distributed around the panel 110, such that the sensor(s) 132 can collectively measure loads and/or forces present on the panel 110. As described above, in some embodiments, the scale assembly 100 can include first and second scales that each include a panel and sensor(s). In such embodiments, the sensor(s) 132 associated with a first scale can be distributed around the panel 110 associated with the first scale, and the sensor(s) 142 associated with a second scale can be distributed around a panel 120 associated with the second scale. The sensor(s) 132, 142 can then be configured to measure forces exerted by the user via the respective feet of the user that are placed on the scales.

In some embodiments, each of the sensor(s) 132 can be independent sensors that monitor changes in loads and/or forces and provide independent signals for analysis. The independent signals provided by the sensors can be used to reduce noise (e.g., by averaging or comparing the independent signals) and/or provide a more accurate measure of weight, BCG, and other physiological characteristics or conditions. In some embodiments, a set of sensor(s) 132 can be coupled to one another, e.g., via a Wheatstone bridge, and provide an output that is representative of the combined signals measured by the sensor(s) 132.

In the case of force sensors, the sensor(s) 132 can be configured to measure forces or loads exerted by the foot or feet of a subject on the panel 110 through its interaction with shaft(s) 134 and/or base(s) 136. Each base 136 can contact a floor or surface on which the scale assembly 100 is supported, and each shaft 134 can be coupled to a base 136 and a respective sensor 132. When a subject places his foot or feet on top of the panel 110, the panel 110 can displace downwardly toward the base(s) 136. Each base 136, being in contact with the floor, can transfer a force corresponding to the displacement of the panel 110 to the shaft 134 coupled to that base 136, which can then transfer this force to a respective sensor 132. The sensor 132 can then measure a force or load associated with the subject based on the forces that are transferred to the sensor 132 via the base 136 and the shaft 134. Further details of the structure of the base 136 and the shaft 134 are provided below.

Each base 136 can be configured to receive, provide mechanical support and/or enclose a portion of a shaft 134, while being in physical contact with an external surface located underneath the scale assembly 100 (e.g., the floor). The base(s) 136 can be made of rubber, plastics, metals, wood and/or a combination thereof. In some embodiments, the base(s) 136 can be rubber boot(s) or plug(s) that provide friction or resistance against the floor, e.g., to prevent undesired movement of the scale assembly 100. In some embodiments, the base(s) 136 can include surface finishes or an outer surface arranged to provide enhanced grip and prevent unwanted movement of the scale assembly 100. In some embodiments, each base 136 can include a cavity or opening that can receive at least a portion of a shaft 134. In other embodiments, each base 136 can be formed integrally with a shaft 134. In some embodiments, the base(s) 136 can be partially disposed within housing 130 but extend through the housing 130 to make contact with a floor. For example, the housing 130 can include one or more orifices through which the base(s) 136 can extend, such that one or more surfaces of the base(s) 136 are in direct contact with the floor underneath the scale assembly 100. In other embodiments, the base(s) 136 can be disposed outside of the housing 130, and shaft(s) 134 coupled to the base(s) 136 can extend from the base(s) 136 through orifice(s) in the housing 130.

The shaft(s) 134 can mechanically couple the base(s) 136 to the sensor(s) 132. In some embodiments, the shaft(s) 134 can be struts, pegs, or the like. In some embodiments, each shaft 134 can include a first portion that is coupled to a sensor 132 and a second portion that is coupled to a base 136. Each shaft 134 can have a constant diameter or a diameter that varies between its two ends (e.g., a larger bottom portion for greater stability/support). In some embodiments, the shaft(s) 134 can be disposed within the housing 130 and/or extend partially through an orifice of the housing 130. The shaft(s) 134 can be made of any suitable material including metals, plastics, ceramics, polymeric materials and or composites.

The surround structure 160 can at least partially border the perimeter of the scale device 100 and provides mechanical support to components of the scale assembly 100. In some embodiments, the surround structure 160 can provide mechanical support to prevent accidental tipping and/or tripping of the scale assembly 100. In some embodiments, the surround structure 160 can have sloped or angled portion, e.g., to avoid causing a trip hazard and/or tipping. The surround structure 160 can be configured to increase the footprint of the scale assembly 100 to provide additional contact surface between the scale assembly 100 and the floor, e.g., to prevent accidental tipping of the scale assembly 100 when, for example, a user steps near the edges of the scale device 100. In some embodiments, the surround structure 160 can be a single component, section, and/or portion that surrounds the various components of the scale assembly 100. In other embodiments, the surround structure 160 can include multiple components, sections, and/or portions that can be coupled together to form one structure that surrounds the components of the scale assembly 100. In some embodiments, the surround structure 160 can include one or more sections disposed between the panel 110 and the panel 120 to provide a separation between and/or to set the distance between the panel 110 and the panel 120. In some embodiments, the surround structure 160 can be integrally formed with one or more housings 130, 140. The surround structure 160 can be made of any suitable material including metal, glass, ceramic, polymer, and/or a combination thereof. In some embodiments, the surround structure 160 can be formed of multiple layers of materials, e.g., an inner layer having more rigidity and an outer layer having anti-slip surface, e.g., to facilitate gripping and/or prevent tipping of the scale assembly 100 or to provide comfort to a user.

In some embodiments, the sensor(s) 132, 142 can include electrode(s) that function as impedance sensor(s). For example, one or more electrode(s) can be disposed on each panel 110, 120 of the scale assembly 100, and the one or more electrode(s) can be configured to send signal(s) to one another to measure impedance. In an embodiment, the sensor(s) 132 can include a first electrode disposed on the panel 110 of the first scale, and the sensor(s) 142 can include a second electrode disposed on the panel 120 of the second scale. The two scales can be electronically coupled such that the first and second electrodes can form a closed-loop current. The first and second electrodes can be operatively coupled to a processor that can receive signals from the first and second sensors to determine an impedance. When the subject places his feet on the first and second electrodes (e.g., when seated at a toilet or standing on the scale assembly 100), the first electrode can send a signal (e.g., a current) to the second electrode, and a resulting voltage can be measured to determine a foot-to-foot impedance of the subject. In some embodiments the scale assembly 100 can include one or more electrode(s) disposed on a single panel of the scale assembly 100. For example, in an embodiment the sensor(s) 132 can include a first and a second electrode disposed on the panel 110. Alternatively, in a different embodiment the sensor(s) 142 can include a first and a second electrode disposed on the panel 120. The first and second electrodes can be electrically separated and/or isolated from each other such that the first electrode can send a signal (e.g., electrical current) to the second electrode and a resulting voltage between the two electrodes can be measured to determine an impedance. The first and the second electrode can be disposed on the panel 110 such that when the subject places his feet on the first and second electrodes (e.g., either one foot on each electrode or one foot on both electrodes), the first electrode can send a signal (e.g., a current) to the second electrode, and a resulting voltage can be measured to determine a foot-to-foot impedance or an impedance across a region of a foot.

In some embodiments, the impedance sensor(s) of the scale assembly 100 can be used together with impedance sensor(s) on a toilet seat to determine an impedance measure for the legs of the subject. For example, a toilet seat, such as the toilet seats described in the '658 patent and the '236 application and incorporated above by reference, can include electrodes that are positioned on the two sides of the seat. In some embodiments, the electrodes on the toilet seat can function in a manner similar to the electrodes on the scale to measure a butt cheek-to-butt cheek impedance (or thigh-to-thigh impedance) of the subject. Alternatively or additionally, the electrodes on the toilet seat can act as passive electrodes that measure a resulting voltage from butt cheek to butt cheek that is induced by the current delivered by the electrodes of the scale. This butt cheek-to-butt cheek impedance can be subtracted from the foot-to-foot impedance obtained by the scale assembly 100 to isolate the impedance of the legs of the subject. For example, the following equation below can be used to determine an impedance of the legs of the subject: $Impedance_{Legs} = Impedance_{Foot-to-Foot} - Impedance_{Butt\ Cheek-to-Butt\ Cheek}$. In some embodiments, the isolated leg impedance can be used to identify whether the subject has peripheral edema. For example, a processor (e.g., an onboard processor, a complementary sensing system, and/or a processor of a separate compute device (see FIG. 2)) coupled to the impedance sensors can be configured to determine that a subject has peripheral edema when the impedance of the legs changes by a predefined percentage and/or amount over time, etc.

In some embodiments, impedance sensor(s) as described herein can be configured to deliver a current having an amplitude ranging from between about 5 µA to about 500 µA, including all values and subranges in-between. In some embodiments, impedance sensor(s) as described herein can be configured to deliver current at a range of frequencies, e.g., from about 5 Hz to about 2 MHz. The impedance sensor(s) can be configured to sweep across frequencies and/or different impedance sensor(s) can operate a different frequencies, e.g., to collect data associated with different parts of the subject. For example, a first set of sensors on the scale assembly 100 can operate within a first range of frequencies or at a first frequency to measure foot-to-foot impedance, and a second set of sensors on a toilet seat can operate within a second range of frequencies or at a second frequency to measure butt cheek-to-butt cheek impedance. In some embodiments, measurements of different impedances (e.g., foot-to-foot impedance, butt cheek-to-butt cheek impedance, thigh-to-thigh impedance) can be completed sequentially, while in other embodiments, measurements of different impedances can be completed at the same time or during overlapping time periods (e.g., using currents with different frequencies).

In some embodiments, the sensor(s) 132, 142 can include electrode(s) that can be used to measure one or more of impedance, percentage body fat, fat mass, bone mass, muscle mass, hydration, as well as other wellness parameters.

Figure 2:
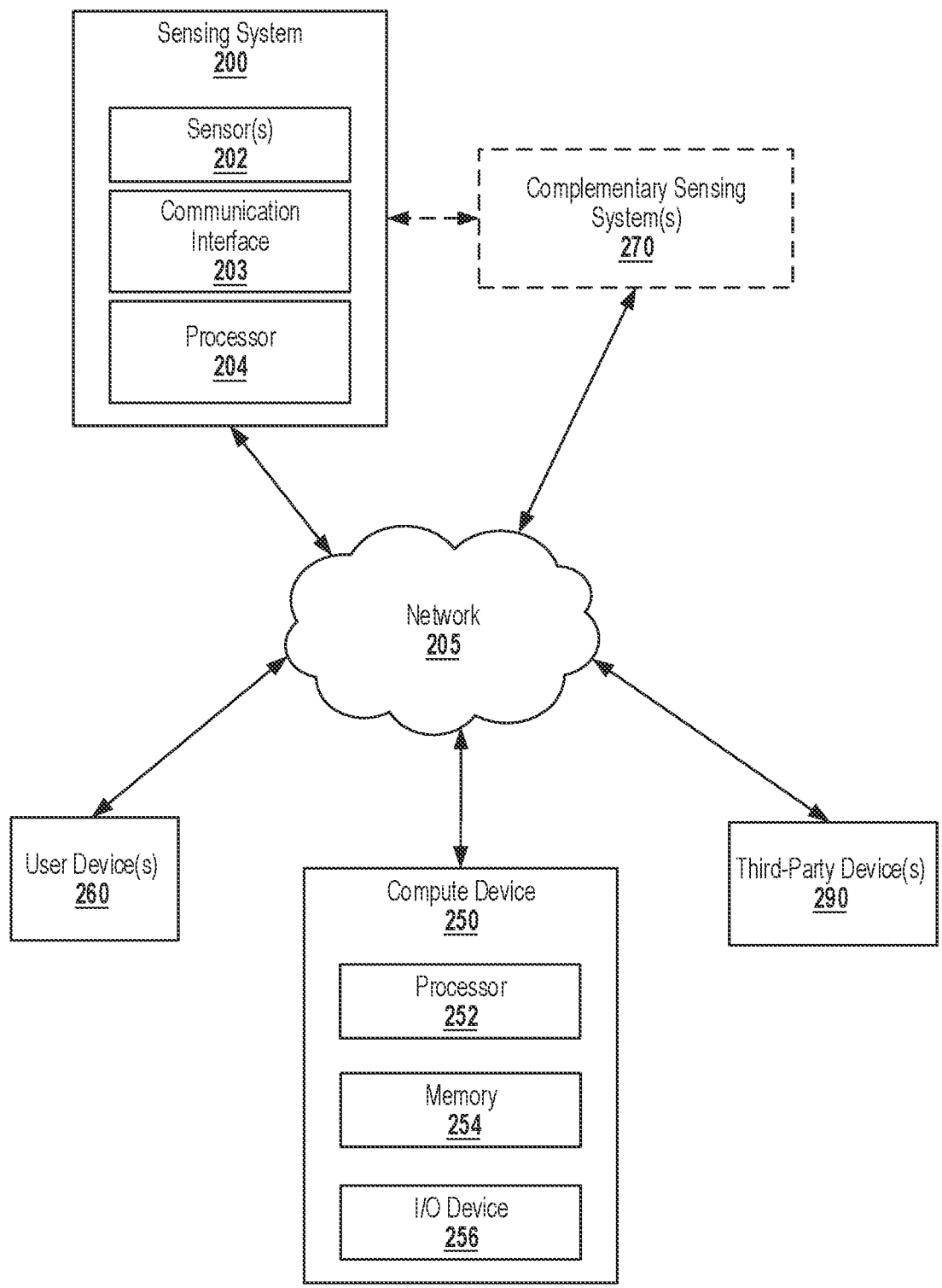
FIG. 2 schematically depicts a network of devices for monitoring physiological conditions of a subject, according to an embodiment.

FIG. 2 depicts a block diagram illustrating a sensing system 200 in communication with other devices via a network 205. In some embodiments, sensing system 200 can be configured to measure physiological data or signals associated with an individual seated on a toilet, including, for example, loads or forces. Sensing system 200 can include component(s) that are structurally and/or functionally similar to those of other sensing systems and devices described herein, including, for example, the scale assembly 100. For example, sensing system 200 can include one or more sensor(s) 202 that can be configured to measure loads or forces. Sensor(s) 202 can be functionally and/or structurally similar to sensor(s) 132, 142. Sensor(s) 202 can be disposed within a scale assembly and configured to collect sensor data representative of loads or forces exerted on the panel by an individual seated on a toilet. The loads or forces measured by the sensor(s) 202 can be indicative of partial weight of the individual seated on the toilet.

In some embodiments, the sensing system 200 can optionally communicate with a complementary sensing system(s) 270 via a network 205. The complementary sensing system(s) 270 can be configured to measure physiological data or signals associated with the same individual as the sensing system 200. For example, an individual can be seated on a toilet seat, and the sensing system 200 implemented as a scale device can measure a first partial weight of the individual and the complementary sensing system 270 integrated into the toilet seat can measure a second partial weight of the individual. In some embodiments, the sensing system 200 and the complementary sensing system 270 can be collectively configured to measure a full body weight of the seated individual. In some embodiments, the sensing system 200 and the complementary sensing system 270 can be configured to determine a posture of the seated individual, e.g., via a distribution of weight between the sensors of the sensing system 200 and the complementary sensing system 270. In some embodiments, the sensing system 200 and the complementary sensing system 270 can be configured to determine different impedance measurements of the seated individual (e.g., foot-to-foot impedance, thigh-to-thigh impedance), and use those different impedance measurements to isolate other impedances of the individual (e.g., leg impedance).

While not depicted, the complementary sensing system(s) 270 can include one or more sensors, communication interfaces, and/or processors for measuring and/or processing data associated with a seated individual. In some embodiments, the complementary sensing system 270 can be configured to receive data (e.g., force data) from the sensing system 200, and an onboard processor of the complementary sensing system 270 can be configured to process and/or analyze this data in combination with other data collected by the complementary sensing system 270 to determine information such as weight, BCG, impedance, or other physiological data or conditions of a subject (e.g., an individual seated on a toilet). In some embodiments, the complementary sensing system(s) 270 can include a sensing system that is integrated into a toilet seat, as described in the '658 patent and '236 application, which have been incorporated by reference above.

In some embodiments, the sensing system 200 can be configured to communicate with other devices, such as a compute device 250, one or more user device(s) 260, one or more third-party device(s) 290, etc., via the network 205. The network 205 can include one or more network(s) that may be any type of network (e.g., a local area network (LAN), a wide area network (WAN), a virtual network, a telecommunications network) implemented as a wired network and/or wireless network and used to operatively couple to any compute device, including sensing system 200, complementary sensing system(s) 270, compute device 250, user device(s) 260, and third-party device(s) 290.

Optionally, the sensing system 200 can be configured to send data measured by sensor(s) 202 via a communication interface 203 to the complementary sensing system(s) 270, the compute device 250, one or more user device(s) 260, and/or one or more third-party device(s) 290. In some embodiments, the sensing system 200 can include onboard processing, such as, for example, a processor 204 implemented as a microprocessor, to process sensor data (e.g., filter, convert, etc.) prior to sending the sensor data to the complementary sensing system(s) 270, compute device 250, one or more user device(s) 260, and/or one or more third-party device(s) 290. Alternatively, sensing system 200 can be configured to send raw sensor data to the complementary sensing system(s) 270, the compute device 250, one or more user device(s) 260, and/or one or more third-party device(s) 290. In some embodiments, processor 204 can be configured to analyze the sensor data and/or determine information such as weight, BCG, impedance, or other physiological data or conditions of a subject (e.g., an individual seated on a toilet). In some embodiments, processor 204 can be configured to present this information to a user, e.g., via an onboard display, audio device, or other output device. In some embodiments, the processor 204 can interface with the communication interface 203 to transmit information to another device (e.g., complementary sensing system 270, user device 260, compute device 250, or third-party device 290) for presenting information to a user. The communication interface 203 can be configured to allow two-way communication with an external device, including, for example, the compute device 250, one or more user device(s) 260, and/or one or more third-party device(s) 290. The communication interface 203 can include a wired or wireless interface for communicating over the network 205.

The compute device 250 can be configured to process and/or analyze the sensor data, e.g., received from the sensor(s) 202. In some embodiments, the compute device 250 can be a nearby compute device (e.g., a local computer, laptop, mobile device, tablet, etc.) that includes software and/or hardware for receiving the sensor data and processing and/or analyzing the sensor data. In some embodiments, the compute device 250 can be a server that is remote from the sensing system 200 but can communicate with the sensing system 200 via network 205 and/or via another device on the network 205 (e.g., a user device 260). For example, sensing system 200 can be configured to transmit sensor data to a nearby device (e.g., a complementary sensing system 270 or a user device 260), e.g., via a wireless network (e.g., Wi-Fi, Bluetooth®, Bluetooth® low energy, Zigbee and the like), and then that device can be configured to transmit the sensor data to the compute device 250 for further processing and/or analysis.

The user device(s) 260 can be compute device(s) that are associated with a user of a toilet equipped with the sensing system 200. Examples of user device(s) 260 can include a mobile phone or other portable device, a tablet, a laptop, a personal computer, a smart device, etc.). In some embodiments, a user device 260 can receive sensor data from the sensing system 200 and process that sensor data before passing the sensor data to the compute device 250. For example, a user device 260 can be configured to reduce noise (e.g., filter, time average, etc.) raw sensor data. In some embodiments, a user device 260 can be configured to analyze the sensor data and present (e.g., via a display) information representative of or summarizing the sensor data. In some embodiments, a user device 260 can provide weight information, body temperature information, heart rate information, etc. to a user. In some embodiments, a user device 260 can transmit the sensor data to the compute device 260, which can analyze the sensor data and send information representative of or summarizing the sensor data back to the user device 260 for presenting (e.g., via a display) to a user.

The third-party device(s) 290 can be compute device(s) associated with other individuals or entities that have requested and/or been provided access to a user's data. For example, the third-party device(s) 290 can be associated with healthcare professionals (e.g., physicians, nurses, therapists) and/or caregivers of the user. The user can select to have certain third parties have access to the user's health data (e.g., including health data obtained from sensor data collected by sensing system 200). The third parties can then track the user's health information to determine whether the user is at risk for certain conditions and/or needs certain interventions, treatments, or care.

The compute device 250 can include a processor 252, a memory 254, and an input/out device (I/O) 256 (or a multiplicity of such components). The memory 254 can be, for example, a random access memory (RAM), a memory buffer, a hard drive, a database, an erasable programmable read-only memory (EPROM), an electrically erasable read-only memory (EEPROM), a read-only memory (ROM), and/or so forth. In some embodiments, the memory 254 stores instructions that cause processor 252 to execute modules, processes, and/or functions associated with processing and/or analyzing sensor data from sensing system 200.

The processor 252 of compute device 250 can be any suitable processing device configured to run and/or execute functions associated with processing and/or analyzing sensor data from sensing system 200. For example, processor 252 can be configured to process and/or analyze sensor data (e.g., received from sensor(s) 202), to determine a weight, BCG, posture, impedance, or other physiological data or conditions of an individual. The processor 242 can be a general purpose processor, a Field Programmable Gate Array (FPGA), an Application Specific Integrated Circuit (ASIC), a Digital Signal Processor (DSP), and/or the like The I/O device 256 of the compute device 250 can include one or more components (e.g. a communication or network interface) for receiving information and/or sending information to other devices (e.g., sensing system 200, user device(s) 260, third-party device(s) 290). In some embodiments, the I/O device 256 can optionally include or be operatively coupled to a display, audio device, or other output device for presenting information to a user. In some embodiments, the I/O device 256 can optionally include or be operatively coupled to a touchscreen, a keyboard, or other input device or receiving information from a user.

While complementary sensing system(s) 270, user device(s) 260, and third-party-device(s) 290 are not depicted with any onboard memory, processing, and/or I/O devices, it can be appreciated that any one of these devices can include components (e.g., a memory, a processor, a I/O device, etc.) that enable it to perform functions such as, for example, processing and/or analyzing the sensor data, or using the sensor data to determine physiological information about an individual (e.g., weight, BCG, posture, impedance, etc.).

Figure 3:
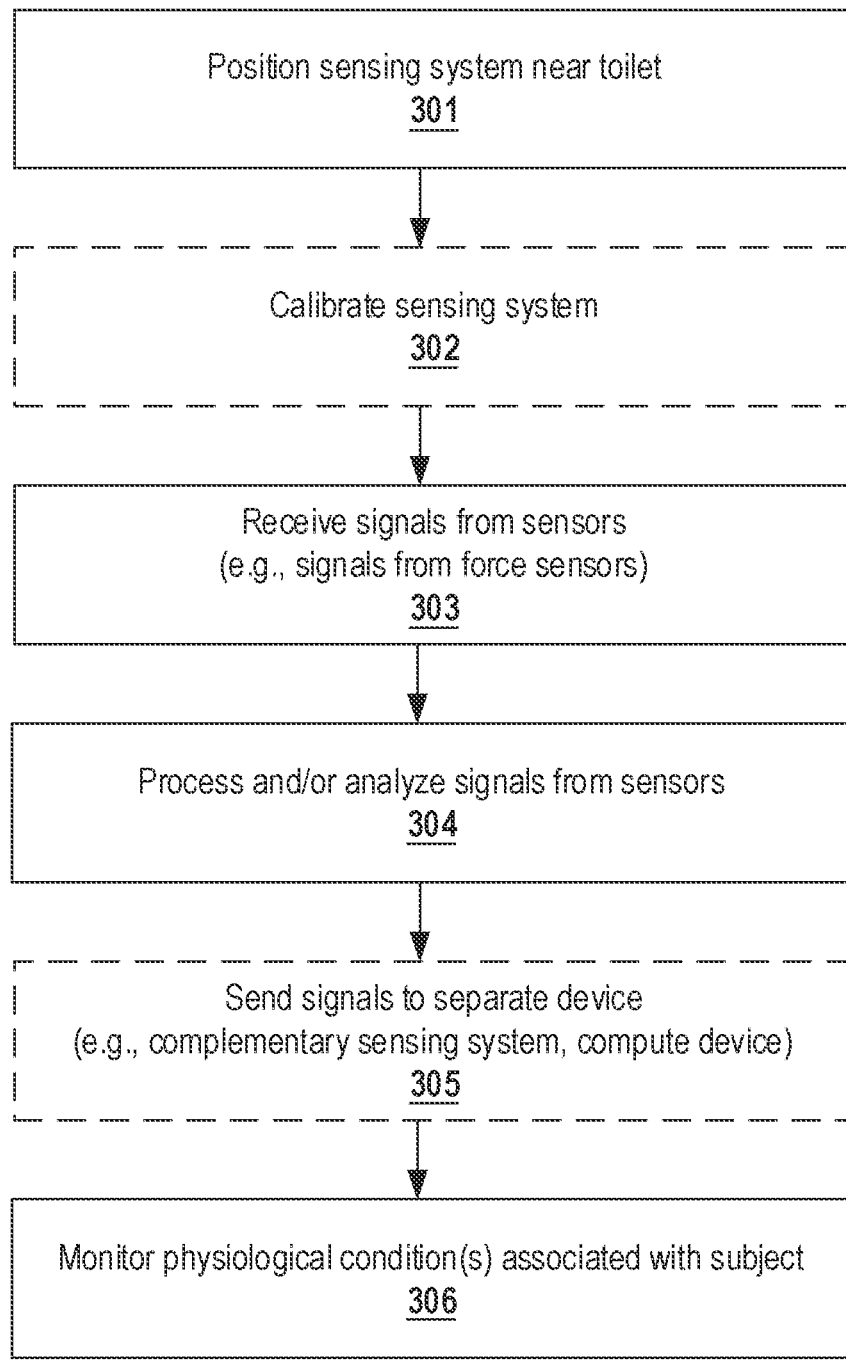
FIG. 3 is a flow chart of an example method of operating a scale device that measures data (e.g., loads or forces) associated with a subject seated on a toilet, according to an embodiment.

FIG. 3 depicts an example method of using systems and devices described herein. A user can place a sensing system or device (e.g., scale assembly 100 or sensing system 200) near to or in front of a toilet, at 301. The sensing system can then be calibrated, at 302, by allowing one or more sensors (e.g., sensor(s) 132, 142, 202) of the sensing system to collect data and send that data to a processor (e.g., onboard processor and/or processor associated with an external compute device (e.g., a complementary sensing system 270, user device 260, compute device 250)) and having the processor calibrate the sensing system. In some instances, the system can be calibrated by first collecting data while a user is not using the scale device, and then collecting data while the user is seated on a toilet and using the scale device. In some embodiments, the system can be calibrated during manufacturing. In some embodiments, the system can be calibrated to a particular user.

Signals can be received from the sensing system (e.g., load and/or force data from one or more force sensors), at 303. The signals can be received when a user sitting on a toilet places his foot or feet on the sensing system, such that the one or more sensors of the sensing system can measure signals exerted by the user's foot or feet on the sensing system. The signals can be indicative of various physiological data of the user. The signals can be processed and/or analyzed by an onboard processor of the sensing system, at 304. Optionally, the signals can be sent to an external device such as a complementary sensing system (e.g., complementary sensing system 270) and/or other compute device (e.g., user device 260, compute device 250), at 305. The complementary sensing system or other compute device can then process and/or analyze the signals from the sensing system. In some embodiments, the data collected by the sensors of the sensing system can be combined with data collected by one or more sensors of the complementary sensing system 270 to determine physiological data associated with the user seated on the toilet. Based on the signals received from the sensing system (and optionally, the complementary sensing system), an onboard processor of the sensing system and/or a processor of an external device can then monitor one or more physiological condition(s) associated with the user, at 306.

FIGS. 4-8 show various views of a sensing system implemented as a scale device or scale assembly 400, according to some embodiments. The scale assembly 400 can include components that are structurally and/or functionally similar to the scale assembly 100 and/or sensing system 200, described above with reference to FIGS. 1 and 2. The scale assembly 400 can include two scales (e.g., a left scale and a right scale) configured to measure forces or loads associated with a subject or individual seated at a toilet or standing on the scale assembly 400. Each scale can operate independently or together and can include components that are structurally and/or functionally similar to the other scale.

Figure 4:
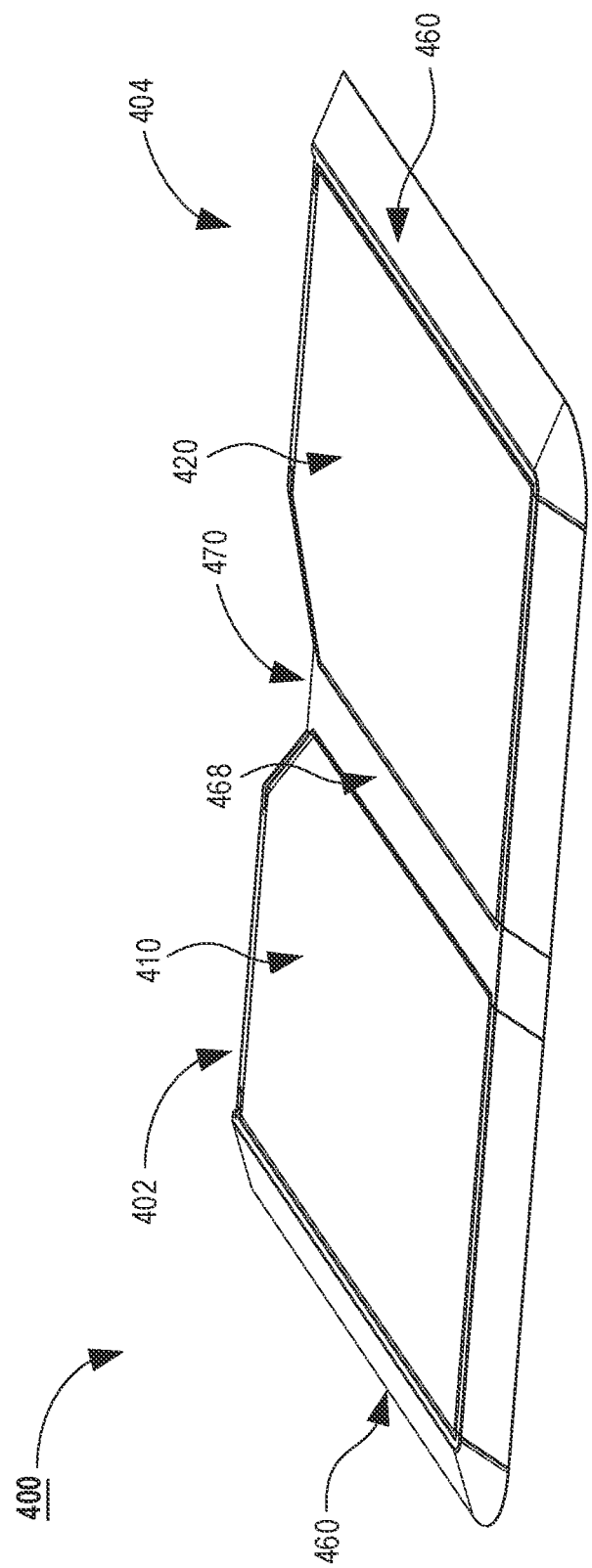
FIG. 4 depicts a perspective view of a scale device for measuring loads or forces associated with a subject seated on a toilet, according to an embodiment.

FIG. 4 depicts a perspective view of the scale assembly 400. The scale assembly 400 can include a first scale 402 having a panel 410 for receiving a first foot of a subject and a second scale 404 having a panel 420 for receiving a second foot of the subject. The first and second scales 402, 404 can be configured to measure forces or loads present on the surface of the panels 410, 420, respectively, when the subject is seated on a toilet and places a foot (e.g., the left or right foot) on top of the each panel 410, 420. A surround structure 460 can be disposed around at least a portion of the first and second scales 402, 404, e.g., to provide support to the panels 410, 420 of the scales, as further described below.

Each scale 402, 404 can include one or more sensors 432, 442, respectively. In some embodiments, the data collected by the sensor(s) 432, 442 (e.g., force data) can be combined with data produced by other sensors such as, for example, force sensor(s), photoplethysmography (PPG) sensor(s), or electrocardiogram (ECG) sensor(s) (e.g., included in a complementary sensing system, such as, for example, complementary sensing system 270). For example, the data collected by sensor(s) 432, 442 in the scale assembly 400 can be combined with data collected by one or more force sensor(s) disposed along a toilet seat to provide a more complete measurement of a weight of a subject seated at a toilet. The sensors disposed along the toilet seat can capture forces exerted by the subject onto the seat, and the sensors 432, 442 disposed in the scale assembly 400 can capture forces exerted by the subject on the scale. The combined data from the seat sensors and the scale sensors 432, 442 can provide a measure that is more representative of a full weight of the subject. In some embodiments, the combined data from the seat sensors and the scale sensors 432, 442 can facilitate determining the posture of the individual seated on the toilet, e.g., based on a distribution of weight across the seat sensors and/or scale sensors 432, 442. In some embodiments, the combined data can be used to estimate relevant information for the medical analysis of cardiac and vascular function. Suitable examples of sensors in toilet seats are described in the '658 patent and the '236 application, incorporated above by reference.

Figure 5:
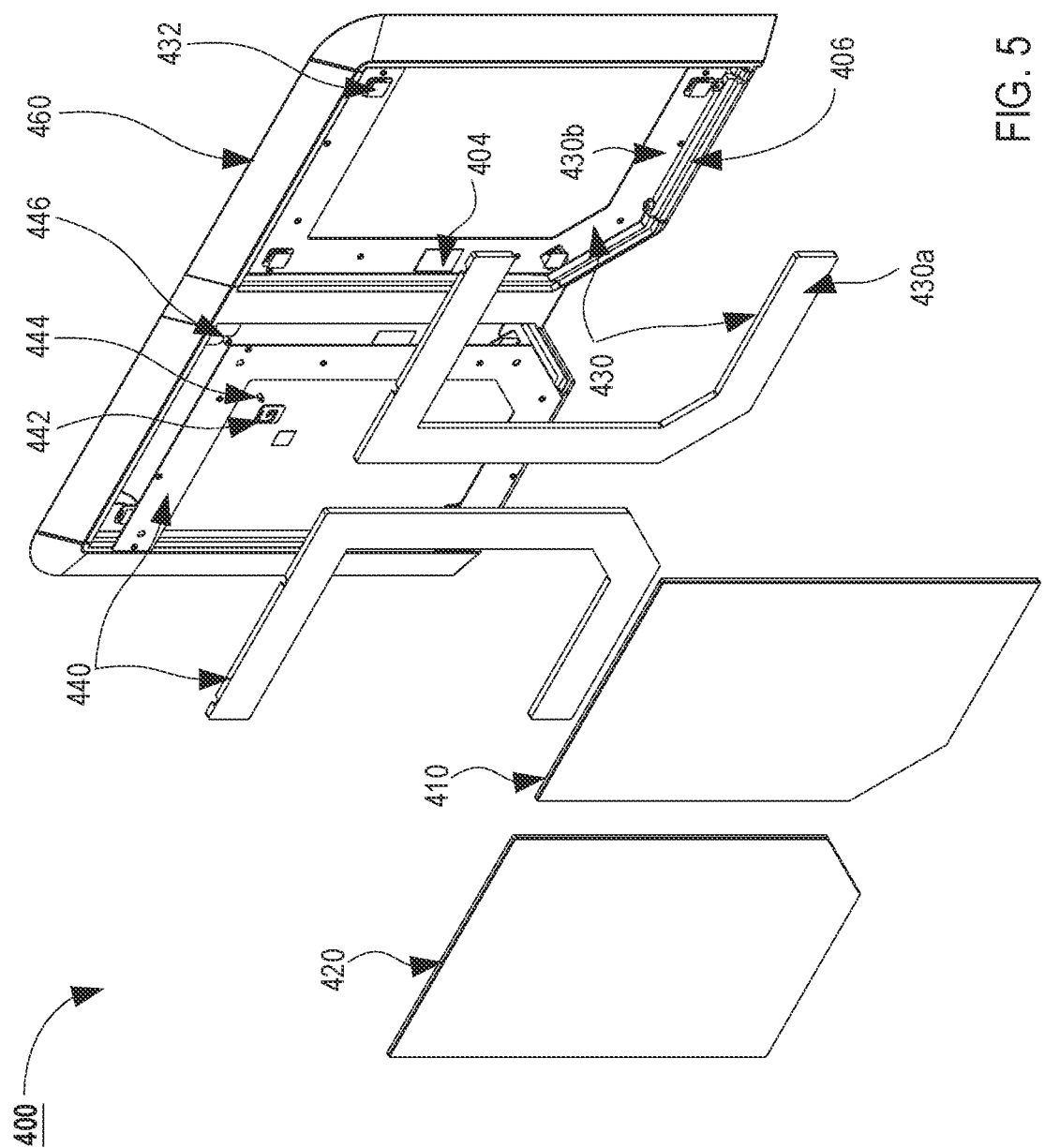
FIG. 5 depicts a partially exploded view of a scale device for measuring loads or forces associated with a subject seated on a toilet, according to an embodiment.

FIG. 5 depicts an exploded view of the scale assembly 400. As shown in FIG. 5, panel 410 is disposed over a housing 430, which can house sensors 432. Similarly, panel 420 is disposed over a housing 440, which can house sensors 442. Each sensor 432 can be coupled to a shaft or strut 434, which in turn can be coupled to and a base 436. Each sensor 442 can be coupled to a shaft or strut 444, which in turn can be coupled to a base 446. The sensors 432, shafts 434, and bases 436 can be structurally and/or functionally similar to the sensors 442, shafts 444, and bases 446. Accordingly, descriptions provided below for one set of such sensors, shafts, and bases are equally applicable to the other.

The panels 410, 420 can have a generally rectangular shape with one cutout corner in an area 470 shaped to fit against a base of a toilet. The area 470 can allow the scale assembly 400 to be placed adjacent to the base of the toilet, as further described with reference to FIG. 9 below. The panels 410, 420 can be sufficiently large to receive a single foot of a subject (e.g., a left foot or right foot). Each panel 410, 420 can be a flat surface. In some embodiments, the flat surface can be textured, e.g., to increase friction or grip against the surface when a user has his or her feet placed on the surface. Alternatively, the flat surface can be smooth. In some embodiments, the panels 410, 420 can be glass plates. In some embodiments, the panels 410, 420 can be formed of a rigid material other than glass, e.g., a plastic, metal, wood and/or a combination thereof.

The panels 410, 420 can bounded along several sides by the surround structure 460, as shown in FIG. 4. Specifically, the panels 410, 420 can be surrounded by the surround structure 460 along the sides of the panels 410, 420 that do not face a toilet. The panels surround structure 460, by surrounding the panels 410, 420 along these sides, can provide support to the panels 410, 420, protect the scales 402, 404 from collision with other objects and or a user's feet, etc. In some embodiments, the surround structure 460 can be formed of multiple components or sections. In some embodiments, the surround structure 460 can be formed of a signal unitary structure (e.g., a molded structure or bonded together structure). The surround structure 460 can include a section 468 that is disposed between the first and second scales 402, 404 that defines a spacing between the first and second scales 402, 404. In some embodiments, the section 468 can be interchanged with other sections that define a range of different spacing between the first and second scales 402, 404, such that a user can select a spacing that is best suited for that user (e.g., given the user's feet position when seated and/or a height of the user). In some embodiments, the section 468 can include adjustability features that allow a user to adjust a width of that section 468 such that the spacing between the first and second scales 402, 404 can be increased or decreased.

The housing 430 can define one or more areas for accommodating (e.g., housing, containing, supporting, etc.) one or more components of the scale 402, including the sensor(s) 432, shaft(s) 434, and base(s) 436. Similarly, the housing 440 can define one or more areas for accommodating one or more components of scale 404, including the sensor(s) 442, shaft(s) 444, and base(s) 446. In some embodiments, each housing 430, 440 can also include one or more compartments that can accommodate one or more auxiliary component(s), such as, for example, a power source or battery (e.g., battery 406) for powering a respective scale 402, 404 or an onboard processor (e.g., processor 404) or receiving and/or processing sensor data from a respective scale 402, 404. In other embodiments, a single housing (e.g., housing 430 or 440) can be configured to contain a single power source or a single processor that is used with both scales 402, 404.

Figure 8:
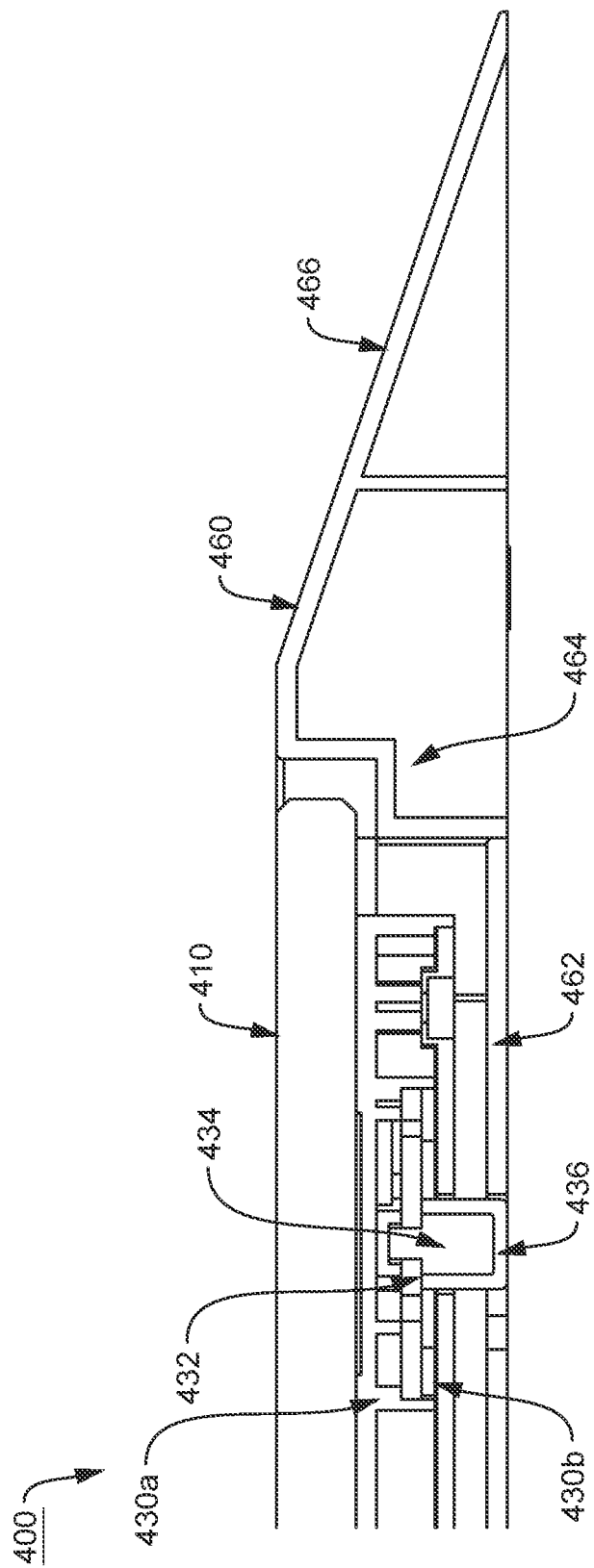
FIG. 8 depicts a cross-sectional view of a portion of a scale device for measuring one or more loads or forces associated with a subject seated on a toilet, according to an embodiment.

As depicted in FIG. 5, the housings 430, 440 can have a bracketed or C-shape, with outer dimensions similar to or smaller than those of the panel 410. In other embodiments, the housings 430, 440 can have a different shape, e.g., a rectangular shape that substantially fills an area beneath each panel 410, 420, respectively. In some embodiments, each housing 430, 440 can include an first C-shape section or cover 430a (e.g., an upper section) and a second C-shape section or cover 430b (e.g., a lower section) that can be coupled together to form the housing 430, 440 e.g., using fasteners, magnets, clamps, etc., as shown in FIGS. 5 and 8. Each housing 430, 440 can be configured to protect the internal components of a scale from external debris, dust, and/or other elements. Each housing 430, 440 can include openings that allow one or more components of the scale to extend out of the housing 430, 440. For example, the housing 430 can include openings along the bottom that allow one or more base(s) 436 to extend out through the housing 430 and contact a surface that the scale assembly 430 is supported on (e.g., a floor or platform in front of a toilet), as shown in FIG. 8.

The sensor(s) 432 can be disposed in the housing 430 and can be configured to measure one or more forces being exerted on the panel 410. Similarly, the sensor(s) 442 can be disposed in the housing 440 and can be configured to measure one or more forces being exerted on the panel 420. The sensor(s) 432, 442 can be structurally and/or functionally similar to the sensor(s) 132 described above with respect to the scale assembly 100. For example, the sensor(s) 432, 442 can be configured to measure parameters that provide information regarding a weight, BCG, or posture of a subject seated at a toilet, e.g., by measuring loads or forces present on the panel 410 due to a weight exerted by the subject's feet on the panel. The sensor(s) 432, 442 can be configured to measure changes in the parameters such as changes in loads and/or forces, which can be used to calculate, for example, a weight change due to defecation or urination. The information collected by the sensor(s) 432, 442 can also be used to determine the forces generated by a heart of the seated individual and provide BCG data for the individual over time. In some embodiments, the sensor(s) 432, 442 can be coupled to a processor (e.g., onboard processor 404 and/or a processor of a complementary sensing system or other external compute device) that can use the information collected by the sensor(s) 432, 442 to evaluate various physiological data or conditions of the individual, including information for the medical analysis of cardiac and vascular function of a seated individual (e.g., stroke volume, cardiac output, weight and/or speed of urination, weight and/or speed of defecation, respiration rate, and more).

Figure 6:
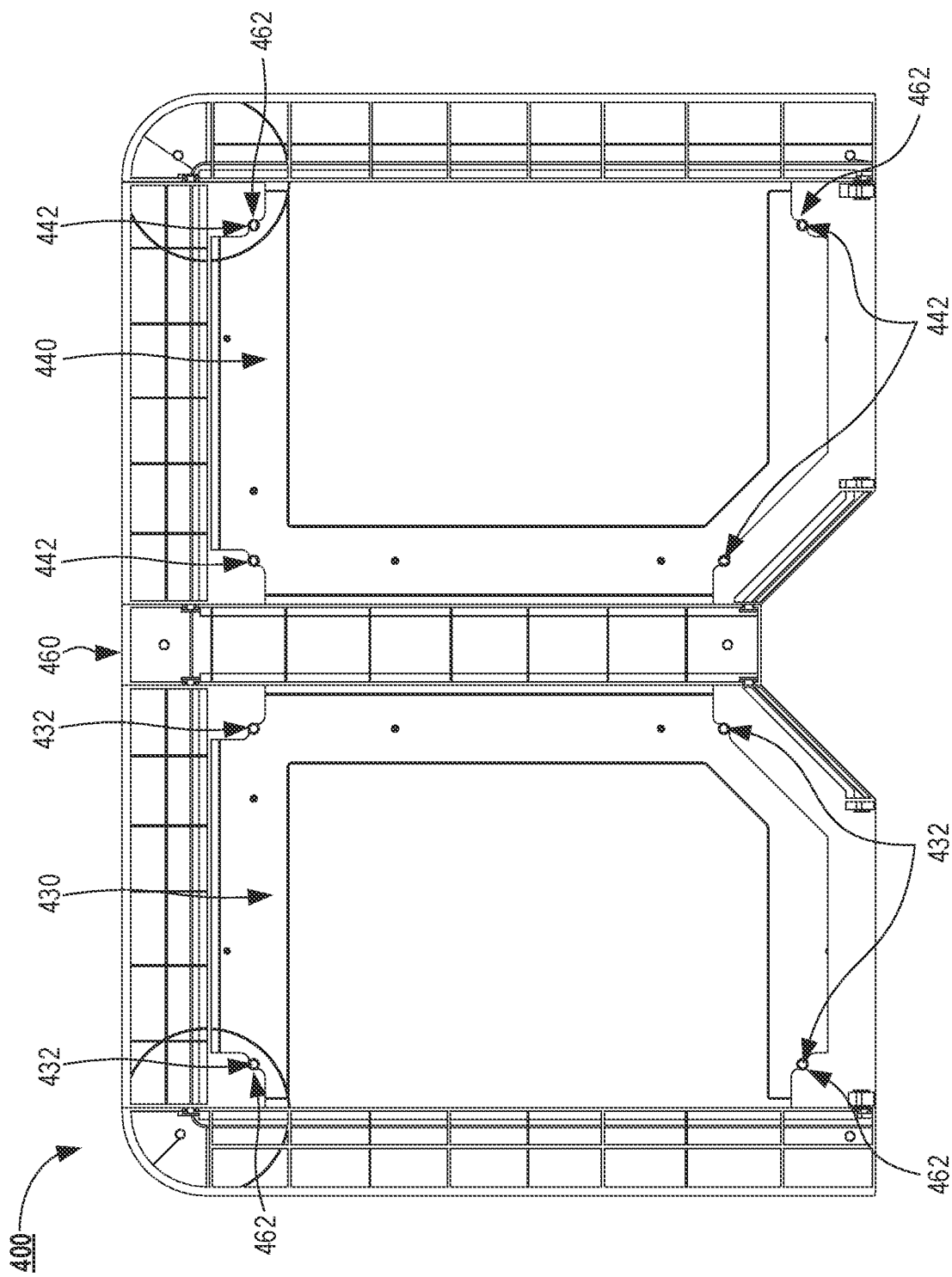
FIG. 6 depicts a bottom view of a scale device for measuring loads or forces associated with a subject seated on a toilet, according to an embodiment.

The sensor(s) 432, 442 can be load and/or force sensor(s) such as load cells (e.g., pneumatic load cells, hydraulic load cells, piezoelectric crystal load cells, inductive load cells, capacitive load cells, magnetostrictive load cells, strain gauge load cells, etc.), strain gages, force sensing resistors (FSR) or printed or flexible force sensors, optical force sensors, etc. The sensor(s) 432, 442 can be distributed about each respective housing 430, 440 to cover the area of the respective panel 410, 420 configured for receiving a single foot of a subject (e.g., a left foot or right foot). In some embodiments, as shown in FIG. 6, the sensor(s) 432, 442 can be located near each one of the corners of their respective C-shaped housings 430, 440. In some embodiments, each of the sensor(s) 432, 442 can be independent sensors that monitor changes in loads and/or forces and provide independent signals for analysis (e.g., by a processor). The independent signals provided by the sensor(s) 432, 442 can be used to reduce noise (e.g., by averaging or comparing the independent signals) and/or provide a more accurate measure of weight, BCG, posture, and other physiological characteristics or conditions. In some embodiments, a set of sensor(s) 432, 442 can be coupled to one another, e.g., via a Wheatstone bridge, and provide an output that is representative of the combined signals measured by that set of sensor(s) 432, 442.

In some embodiments, the data collected by the sensor(s) 432, 442 can be combined or analyzed with data produced by other sensors such as, for example, force sensors included in a complementary sensing system. For example, the data collected by sensor(s) 432, 442 in the scale assembly 400 can be combined with data collected by one or more force sensor(s) disposed along a toilet seat to provide a more complete measurement of a weight of a subject seated at a toilet. The sensors disposed along the toilet seat can capture forces exerted by the subject onto the seat, and the sensors disposed in the scale assembly 400 (e.g., sensor(s) 432, 442) can capture forces exerted by the subject onto the scale. The combined data from the seat sensors and the scale sensors can provide a measure that is more representative of a full weight of the subject. In some embodiments, the combined data can be used to estimate relevant information for the medical analysis of cardiac and vascular function, as well as to determine a posture of the seated subject.

Figure 7:
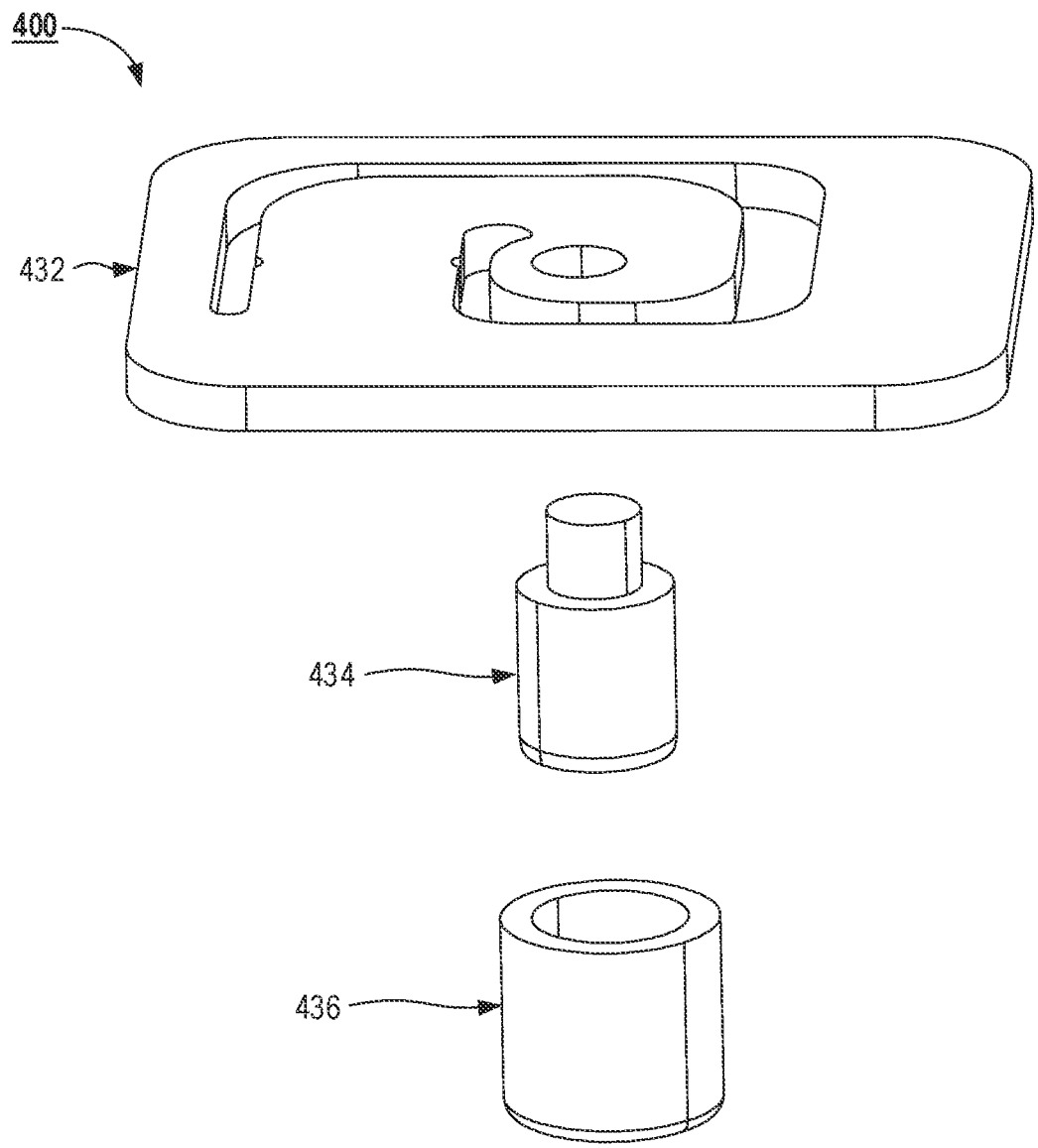
FIG. 7 depicts an exploded view of a sensor assembly for detecting loads or forces on a scale device, according to an embodiment.

The sensor(s) 432 can be configured to measure forces or loads exerted by the foot or feet of a subject on the panel 410 through its interaction with shaft(s) 434 and/or base(s) 436. Similarly, the sensor(s) 442 can be configured to measure forces or loads exerted by the foot or feet of a subject on the panel 420 through its interaction with shaft(s) 444 and/or base(s) 446. Each base 436, 446 can contact a floor or surface on which the scale assembly 400 is supported, and each shaft 434, 444 can be coupled to a base 436, 446 and a respective sensor 432, 442. An exploded view of this arrangement is shown in FIG. 7, and a cross-sectional view of these components is shown in FIG. 8. When a subject places a foot on top of a panel 410, 420, that panel 410, 420 can displace downwardly toward the respective bases 436, 446. Each base 436, 446, being in contact with the floor, can transfer a force corresponding to the displacement of the panel 410, 420 to the shaft 434, 444 coupled to that base 436, 446, which can then transfer this force to a respective sensor 432, 442. The sensor 432, 442 can then measure a force or load associated with the subject based on the forces that are transferred to the sensor 432, 442 via the base 436, 446 and the shaft 434, 444.

Each base 436, 446 can be configured to receive, provide mechanical support and/or enclose a portion of a respective shaft 434, 444 while being in physical contact with an external surface located underneath the scale assembly 400 (e.g., the floor). As shown in FIG. 8, each base 436 includes a cavity or opening sized and configured to receive at least a portion of a shaft 434. The base 436 can be partially disposed in the housing 430 and extend through an opening in the housing 430 to make contact with a floor underneath the scale assembly 400. In some embodiments, each base 436, 446 can be implemented as a rubber boot.

FIG. 8 shows that each shaft 434 can mechanically couple a base 436 to a sensor 432. Each shaft 434 includes a first portion that is coupled to a sensor 432 and a second portion that is coupled to a base 436. The first portion of each shaft 434 can have substantially cylindrical shape characterized by a first diameter sized and configured to fit through an opening or into an orifice of the sensor 432. The second portion of each shaft 434 can have a cylindrical shape characterized by a second diameter sized and configured to fit within the cavity or opening of in the base 436. In some embodiments, the second diameter can be larger than the first diameter, e.g., to provide greater support along the base(s) 436 of the scale 402. The shaft(s) 434, 444 can be made of any suitable material including metals, plastics, ceramics, polymeric materials and or composites.

The surround structure 460 can partially border the perimeter of the scales 402, 404. The surround structure 460 can be made of any suitable material including metal, glass, ceramic, polymer, and/or a combination thereof. In some embodiments, the surround structure 460 can be formed of multiple layers of materials, e.g., an inner layer having more rigidity and an outer layer having anti-slip surface, e.g., to facilitate gripping and/or prevent tipping of the scale assembly 400 or to provide comfort to a user. The surround structure 460 can have a sloped or angled portion 466 configured to avoid causing a trip hazard. The surround structure 460 can also include one or more features for providing support to components of the scales 402, 404. For example, the surround structure 460 can include a ledge or extension 464 (depicted in FIG. 8) which can prevent tipping of the panels 410, 420, e.g., when a user steps on a corner or edge of the panels 410, 420. The ledge 464 can be designed to not interfere with the panels 410, 420 during use of the scales 402, 404 (e.g., the ledge 464 can be spaced from the panel 410, 420 so as to not cause any forces from the panels 410, 420 to be transferred to the surround structure 460), but should a particular panel 410, 420 tip, the ledge 464 can be configured to catch that panel to prevent tipping of the panel. Additionally or alternatively, the surround structure 460 can be configured to prevent movement or shifting of the bases 436, 446. As depicted in FIGS. 6 and 8, the surround structure 460 can include sections 462 that partially bound the bases 436, 446 and prevent them from shifting, tilting, etc. during use. The sections 462 can be flat sections that extend partially underneath the housings 430, 440 to partially surround the bases 436, 446.

In some embodiments, the scale assembly 400 can include additional sensor(s), e.g., impedance sensors such as electrodes, that can be used to measure an impedance of the subject. For example, a first electrode can be disposed on the panel 410, and a second electrode can be disposed on the panel 420. When the subject places his feet on the first and second electrodes (e.g., when seated at a toilet or standing on the scale assembly 400), the first electrode can send a signal (e.g., a current) to the second electrode, and a resulting voltage can be measured to determine a foot-to-foot impedance of the subject. In other embodiments, the scale assembly 400 can include one or more electrodes disposed on a single panel. For example, in an embodiment the scale assembly 400 can include a first and second electrodes disposed on the panel 410. Alternatively, in a different embodiment the scale assembly 400 can include a first and second electrodes disposed on the panel 420. The first and second electrodes can be electrically separated and/or isolated from each other such that the first electrode can send a signal (e.g., electrical current) to the second electrode and a resulting voltage between the two electrodes can be measured to determine an impedance. The first and the second electrode can be disposed on the panel 410 such that when the subject places his feet on the first and second electrodes (e.g., either one foot on each electrode or one foot on both electrodes), the first electrode can send a signal (e.g., a current) to the second electrode, and a resulting voltage can be measured to determine a foot-to-foot impedance or an impedance across a region of a foot. In some embodiments, the impedance sensor(s) of the scale assembly 400 can be used together with impedance sensor(s) on a toilet seat to determine an impedance measure for the legs of the subject, as described above with reference to FIG. 1.

Figure 9:
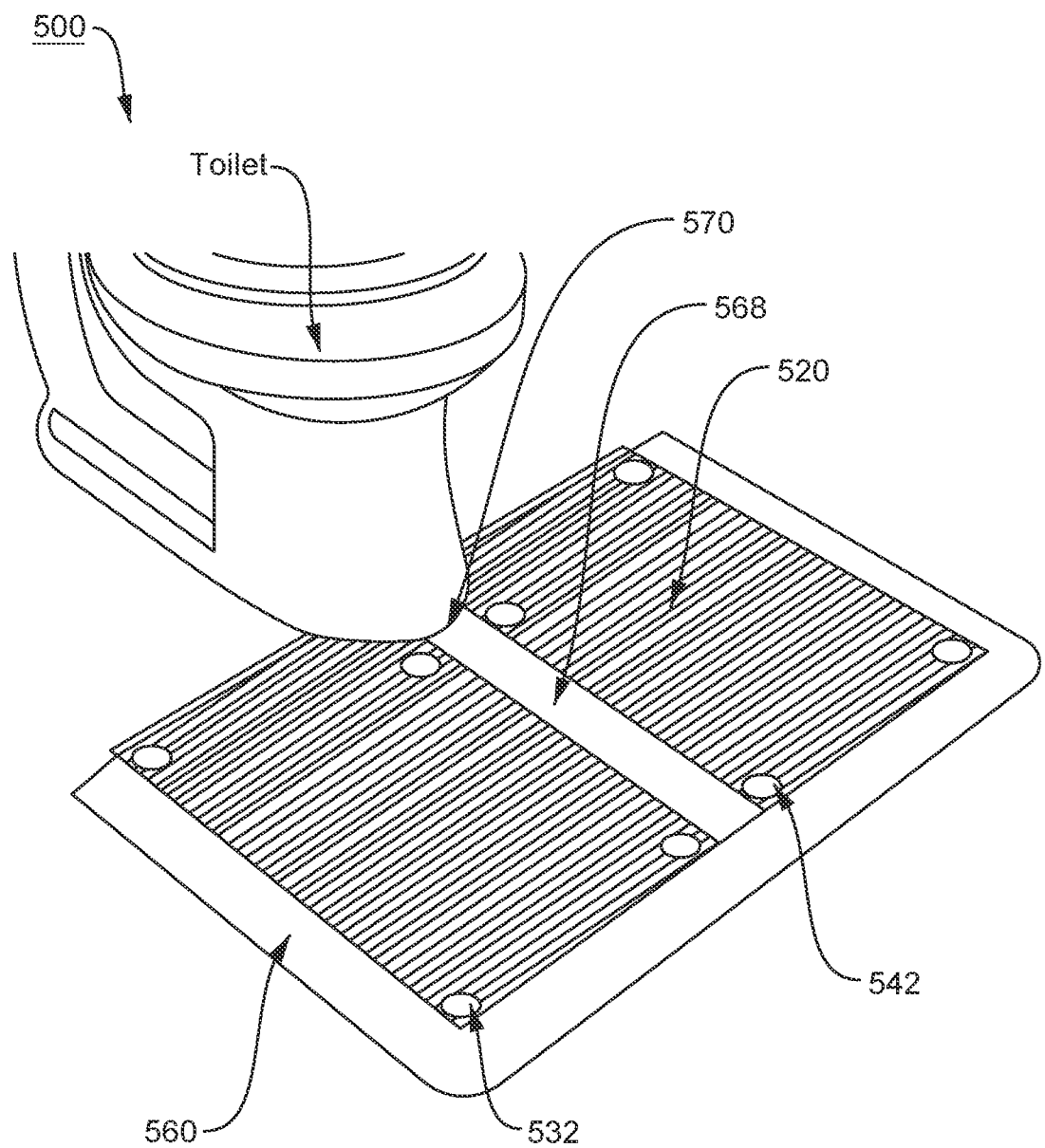
FIG. 9 depicts a perspective view of a portion of a toilet and a scale device positioned adjacent to the toilet for measuring loads or forces associated with a subject seated on a toilet, according to an embodiment.

FIG. 9 is a schematic illustration of a sensing system implemented as a scale assembly 500, according to some embodiments. The scale assembly 500 can include components that are structurally and/or functionally similar to other scale assemblies and sensing systems described herein, e.g., scale assembly 100, 400. For example, the scale assembly 500 can include two scales configured to measure forces or loads associated with a subject seated at a toilet or standing on the scale assembly 500. Each scale can operate independently and can include components that are structurally and/or functionally similar to the other scale. In some embodiments, the scale assembly 500 can be used in conjunction with a sensing system associated with a toilet seat, e.g., such as any of the sensing devices or systems described in the '658 patent and the '236 application, incorporated above by reference.

FIG. 9 depicts the scale assembly 500 positioned up against a side of a toilet. Similar to the scale assembly 400, the scale assembly 500 can include an area 570 (e.g., a convex area) that is shaped to mate with a corresponding portion of a base of the toilet. The scale assembly 500 can include first and second panels 510, 520, where a subject seated on the toilet would place his feet. The scale assembly can include sensor(s) 532, 542 that are positioned at various locations beneath the panels 510, 520 for measuring signals exerted on the panels 510, 520 when the subject's feet are placed on the panels 510, 520.

The first and second scales can partially bounded by a surround structure 560. The surround structure can be functionally and/or structurally similar to the surround structure 160 and/or 460. For example, the surround structure 560 can have sloped or angled portion configured to avoid causing a trip hazard. The surround structure 560 can include one or more sections 568 disposed between the panel 510 and the panel 520 to provide a separation between and/or to set the distance between the panel 510 and the panel 520 (and therefore the respective scales), as shown in FIG. 9. The surround structure 560 can be made of any suitable material including metal, glass, ceramic, polymer, and/or a combination thereof. The surround structure 560 can be configured to increase a grip on a surface in front of a toilet, e.g., to prevent movement of the scale during use. In some embodiments, the surround structure 560 can be formed of multiple layers of materials, e.g., an inner layer having more rigidity and an outer layer having anti-slip surface, e.g., to facilitate gripping and/or prevent tipping of the scale assembly 500 or to provide comfort to a user.

FIGS. 10-14 depict another example of a scale assembly 600, according to embodiments. The scale assembly 600 can include components that are structurally and/or functionally similar to other scale assemblies described herein, including, the scale assemblies 100, 400, 500, described above. The scale assembly 600 can include multiple scales, such as a left scale 604 and a right scale 602, configured to measure forces or loads associated with a subject or individual seated at a toilet or standing on the scale assembly 600. Each scale 602, 604 can operate independently or together and can include components that are structurally and/or functionally similar to the other scale.

Figure 12:
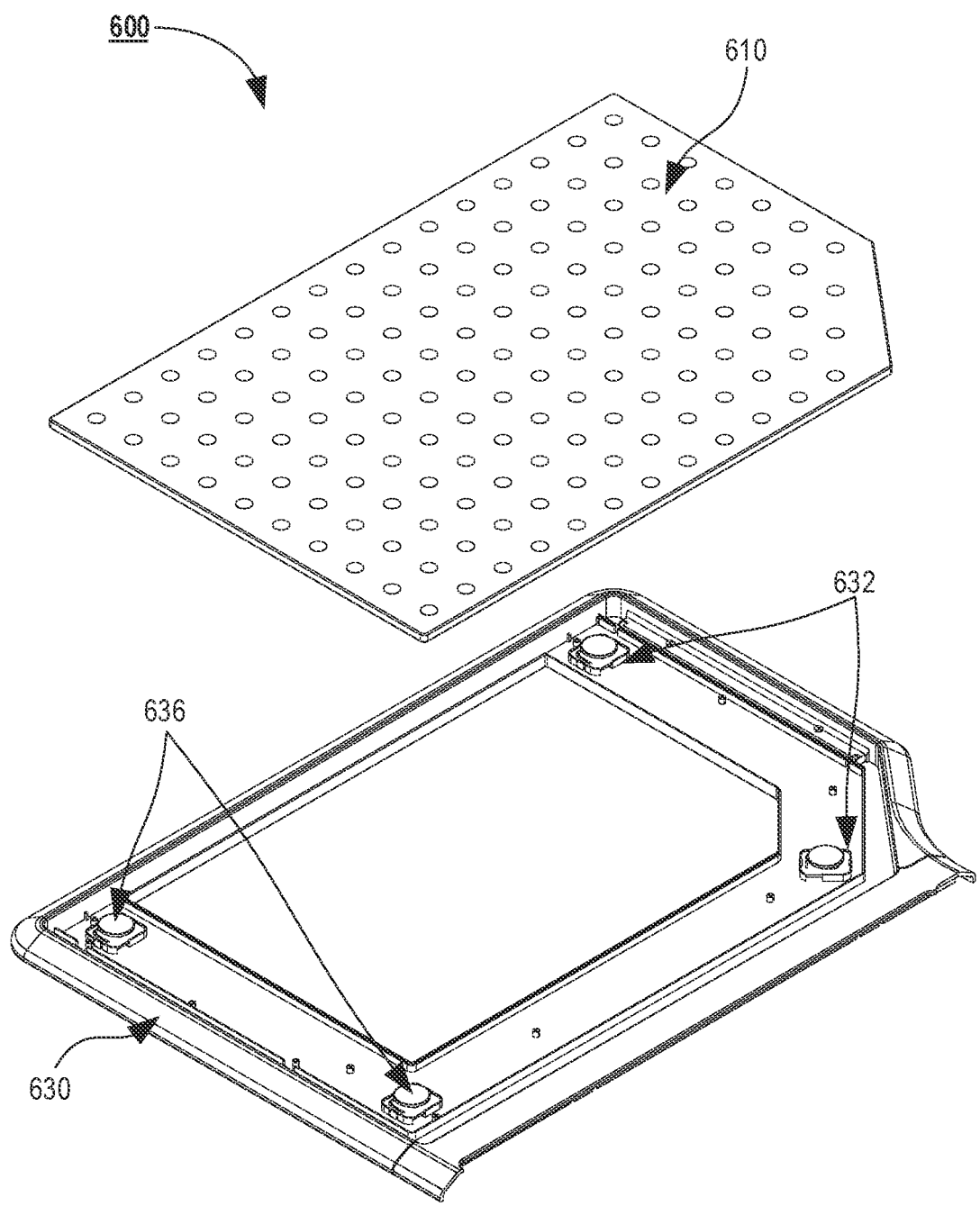
FIG. 12 depicts a partially exploded view of the scale device depicted in FIG. 10.
Figure 13:
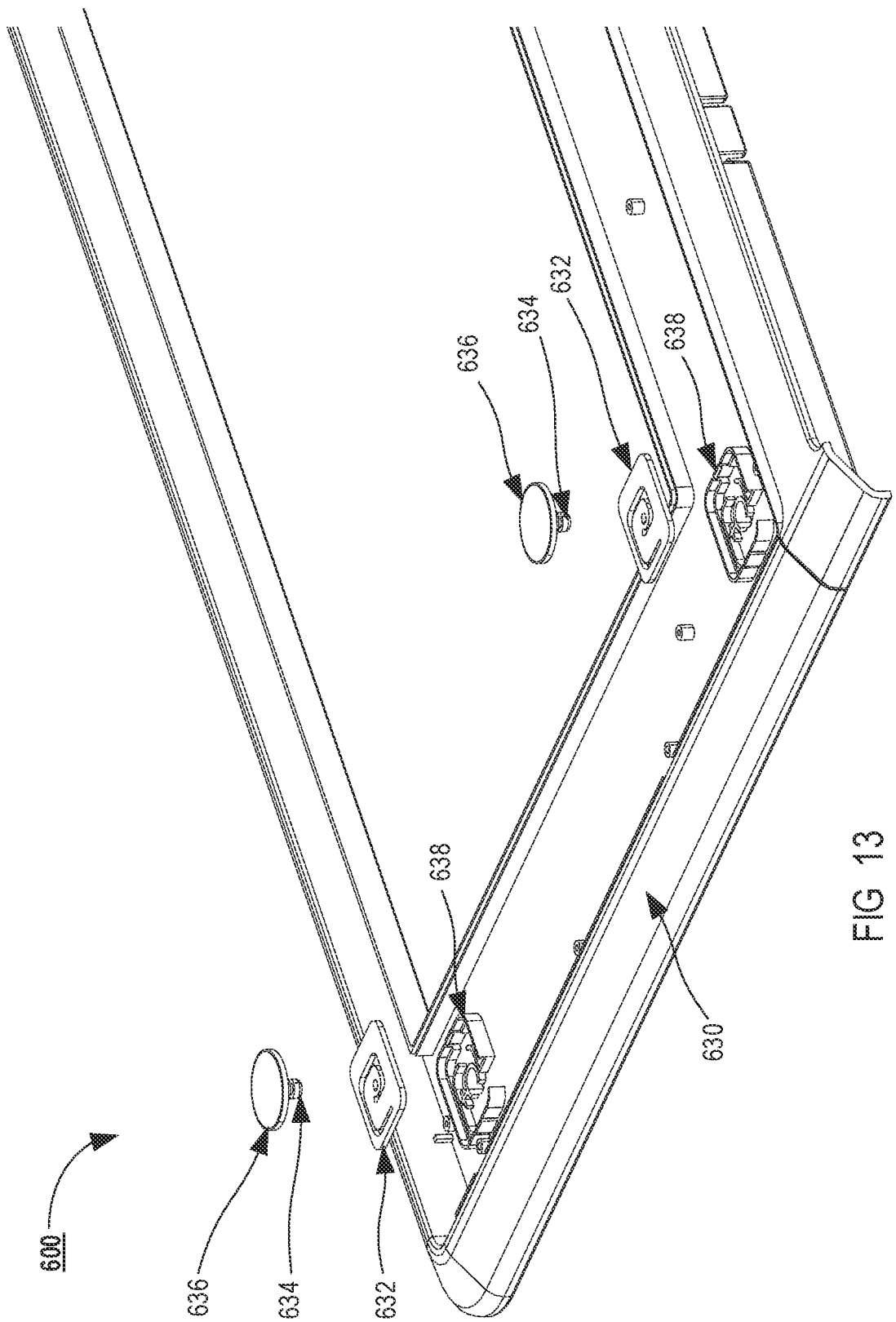
FIG. 13 depicts an enlarged exploded view of a sensor assembly of the scale device depicted in FIG. 10.
Figure 14:
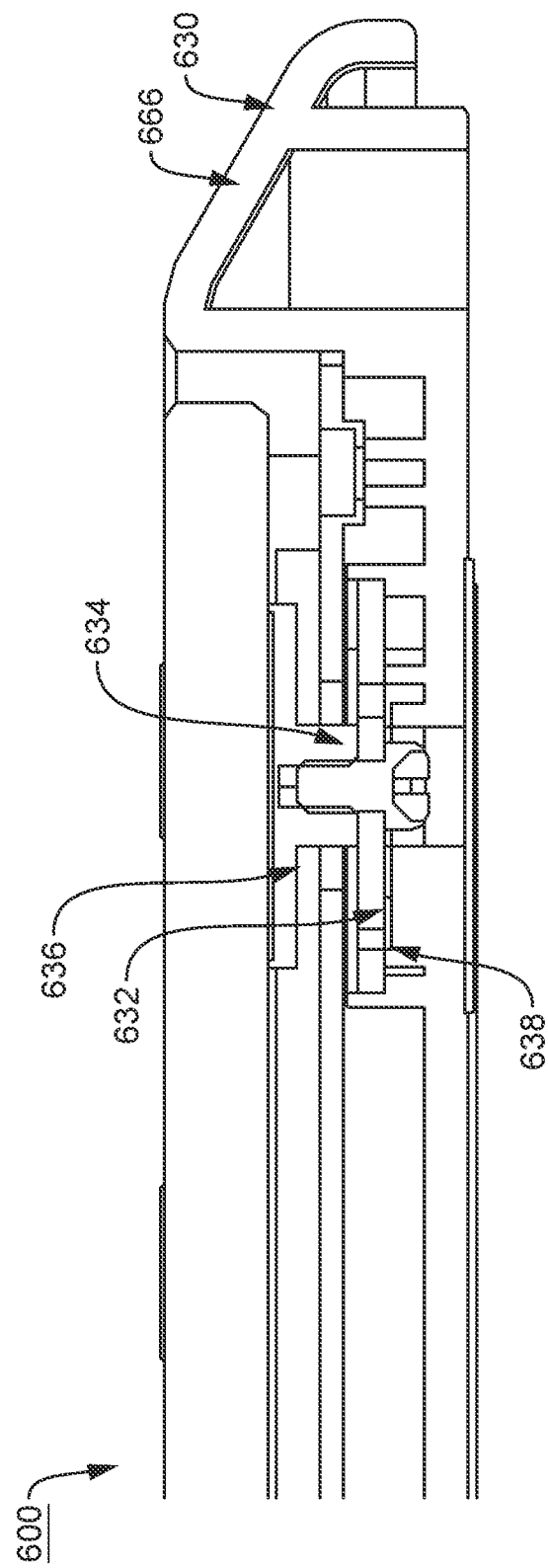
FIG. 14 depicts a cross-sectional view of a portion of the scale device depicted in FIG. 10.

Each scale 602, 604 can include sensors 432, as shown in FIGS. 12-14. The sensors 632 can be configured to measure forces present on a surface of the panels 610, 620 of the scales 602, 604. In some embodiments, the data collected by the sensors 432 (e.g., force data) can be combined with data collected by other sensors, such as, for example, data from sensors located on a toilet seat. As described above, in some embodiments, the sensors 432 in combination with sensors on a toilet seat can be configured to provide data that is more representative of a full weight of a subject. Suitable examples of sensors in toilet seats are described in the '658 patent and the '236 application, incorporated above by reference. In some embodiments, the scale assembly 600 can include additional sensor(s), e.g., impedance sensors such as electrodes, that can be used to measure an impedance of the subject.

Each scale 602, 604 can include a housing or frame 630, 640, respectively, that can house sensors 632, along with other components of the scale assembly 600. For example, the housing 630, 640 can house onboard power sources (e.g., batteries), processors, etc. Each housing 630, 640 can include a surround structure that is integrated with the housing 630, 640. The surround structure can include features that are structurally and/or functionally similar to other surround structures described herein, including surround structures 160, 460, 560. For example, the surround structure can include a sloped or angled portion 666, and the surround structure (and/or other portions of the housings 630, 640) can be formed of multiple layers of materials, e.g., an inner layer having more rigidity and an outer layer having anti-slip surface.

Figure 11:
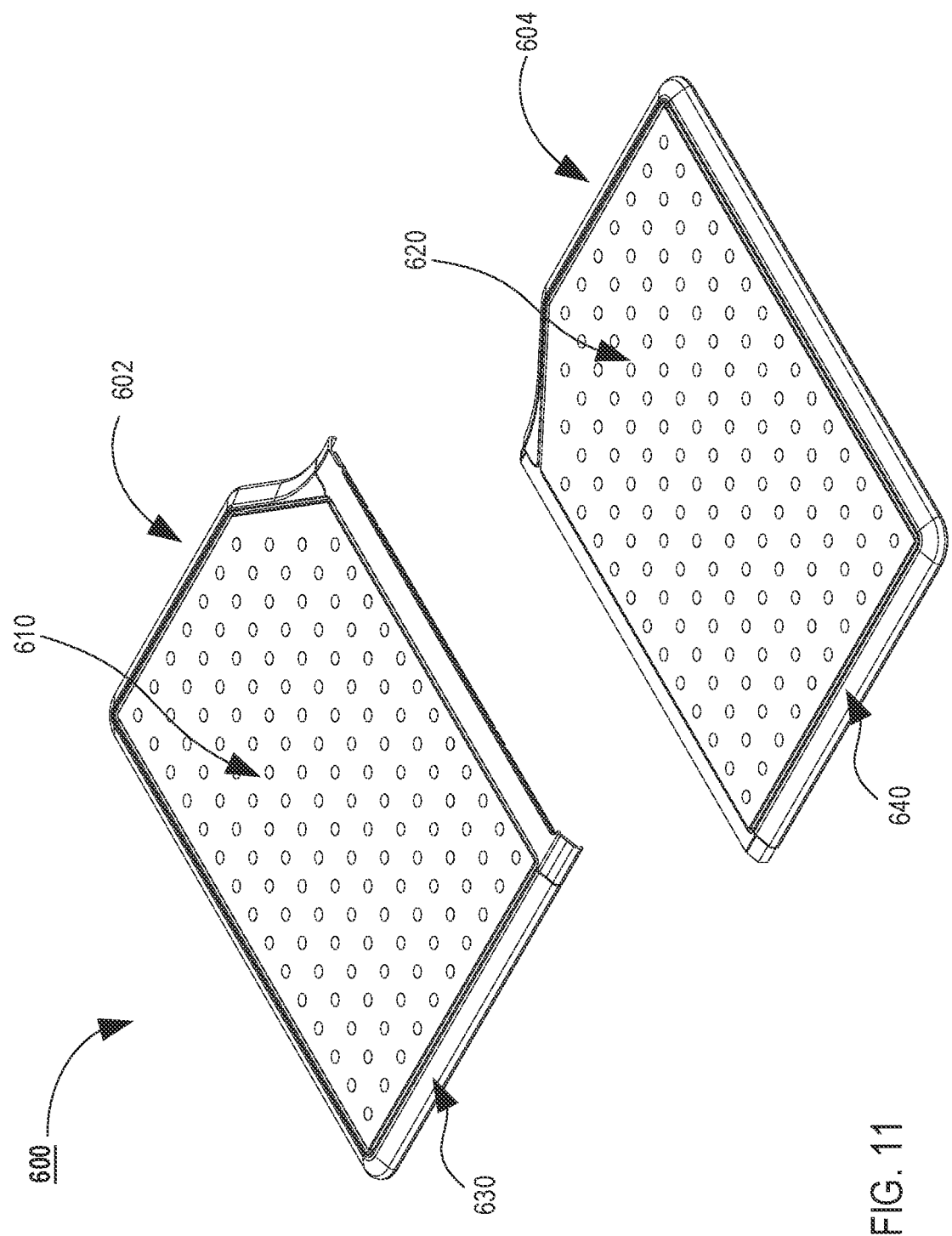
FIG. 11 depicts a partially deconstructed view of the scale device depicted in FIG. 10.

The housings 630, 640 can be configured to disengage or decouple from one another, as depicted in FIG. 11. In some embodiments, the housings 630, 640 can include mating features along their coupling point to facilitate coupling of the housings 630, 640 together. For example, the housings 630, 640 can include grooves, recesses, etc. along with mating ledges, protrusions, etc. that allow the housings 630, 640 to snap and/or lock together. In some embodiments, one or both of the housings 630, 640 can include locking elements (e.g., latches, clamps, sliders, etc.) that can lock the housings 630, 640 together and/or be released to decouple the housings 630, 640. In some embodiments, the housings 630, 640 can include electrical couplings that join electrical components in the two scales 602, 604 together when the housings 630, 640 are coupled to each other. In some embodiments, the housings 630, 640 can be integrally formed as a single component and/or permanently coupled (e.g., using adhesive and/or mechanical fasteners). When the housings 630, 640 are coupled together, a section 668 of one or both housings 630, 640 can define a predetermined spacing between the two scales 602, 604. In some embodiments, additional attachments can be coupled to the housings 630, 640 to change the spacing between the two scales 602, 604.

When the housings 630, 640 are coupled together, the housings 630, 640 can collectively define an area or shape 670 that is shaped to mate with a corresponding portion of a base of a toilet. Accordingly, the scale assembly 600, once assembled, can be configured to sit along a front of a toilet. An individual seated at the toilet can then naturally place his feet on the scale assembly 600, and the sensors 632 of the scale assembly 600, along with any other sensors on the toilet (e.g., sensors along the toilet seat and/or hinge coupling the toilet seat to the toilet base) can measure forces exerted by the individual on the scale assembly 600 and/or toilet.

While two housings 630, 640 are depicted, it can be appreciated that more than two housings 630, 640 can be used without departing from the scope of the disclosure.

Figure 10:
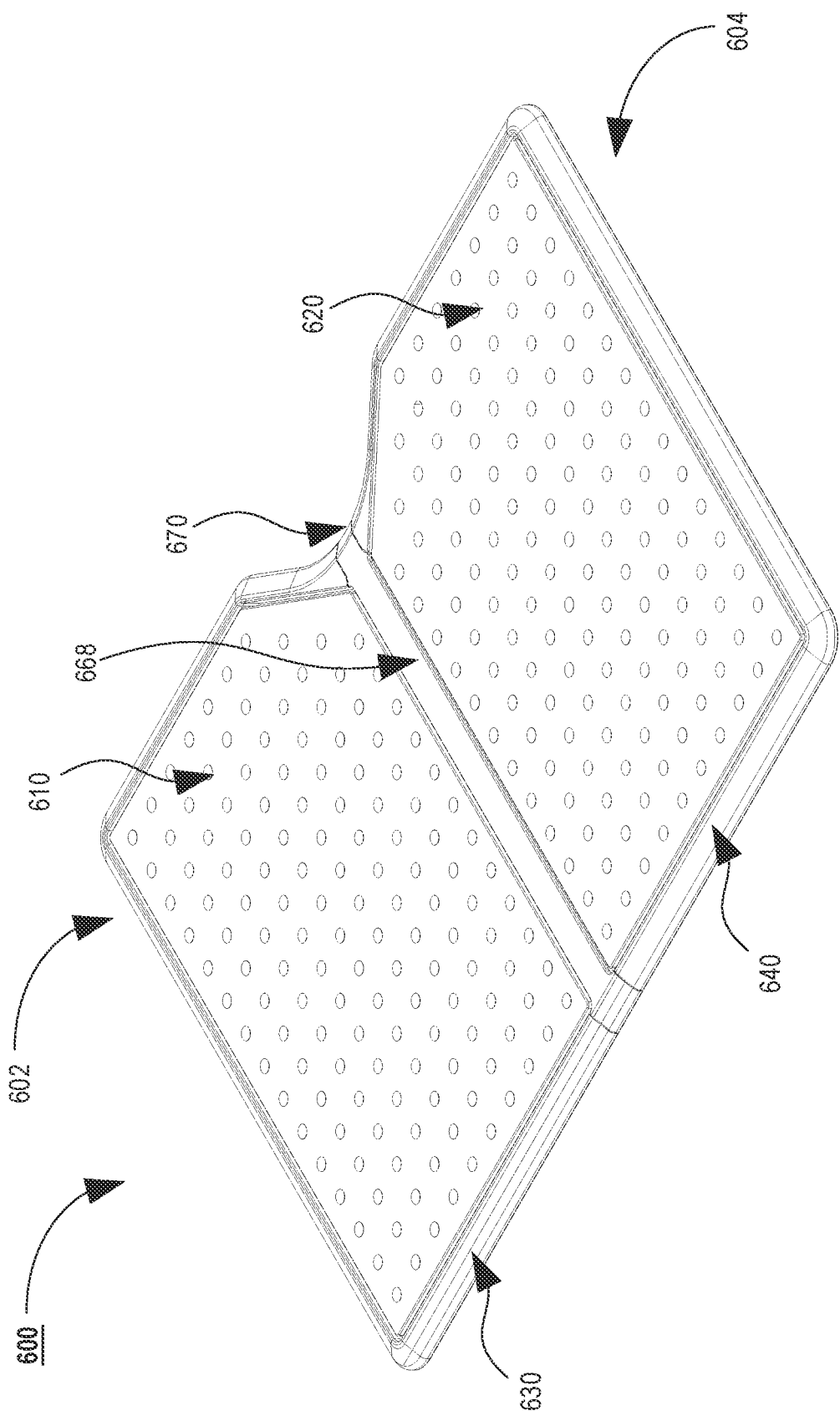
FIG. 10 depicts a perspective view of a scale device for measuring loads or forces associated with a subject seated on a toilet, according to an embodiment.

The housings 630, 640 can support the panels 610, 620, respectively. The panels 610, 620 can be structurally and/or functionally similar to other panels described herein, including panels 110, 120, 410, 420, 510, 520. For example, the panels 610, 620 can be sized to receive a foot (e.g., a right foot or a left foot) of a user. The panels 610, 620 can include texture and/or patterns, as depicted in FIGS. 10 and 11, e.g., that provide friction and/or grip when a user has placed his feet on the panels 610, 620. In some embodiments, the texture and/or patterns can include a plurality of protrusions (e.g., circular protrusions) that are disposed on a top surface of the panels 610, 620. In some embodiments, the scale assembly 600 can include one or more removable layers that are placed on top of the panels 610, 620 to increase friction and/or grip or to thermally isolate a subject's feet from the panels 610, 620. In such embodiments, the panels 610, 620, the panels can be formed of rigid material with a smooth top surface, e.g., such as glass panels.

In some embodiments, the panels 610, 620 can be coupled to the housings 630, 640, respectively, in a fixed or permanent engagement. In some embodiments, the panels 610, 620 can be placed on the housings 630, 640, respectively, and be removable, e.g., to facilitate cleaning and/or repair of components within the housings 630, 640. FIG. 12 provides an exploded view of a right portion of the scale assembly 600, showing how the panel 610 can fit into the housing 630. The housing 630 (and similarly the housing 640, while not depicted in FIG. 12) can include openings that expose a set of pads or plates 636, which can engage directly with the panel 610 when the panel 610 is coupled to the housing 630. The pads 636 can be coupled to or include extensions 634 (e.g., a shaft, strut, etc.) that extend downward onto the sensors 632.

Figure 15:
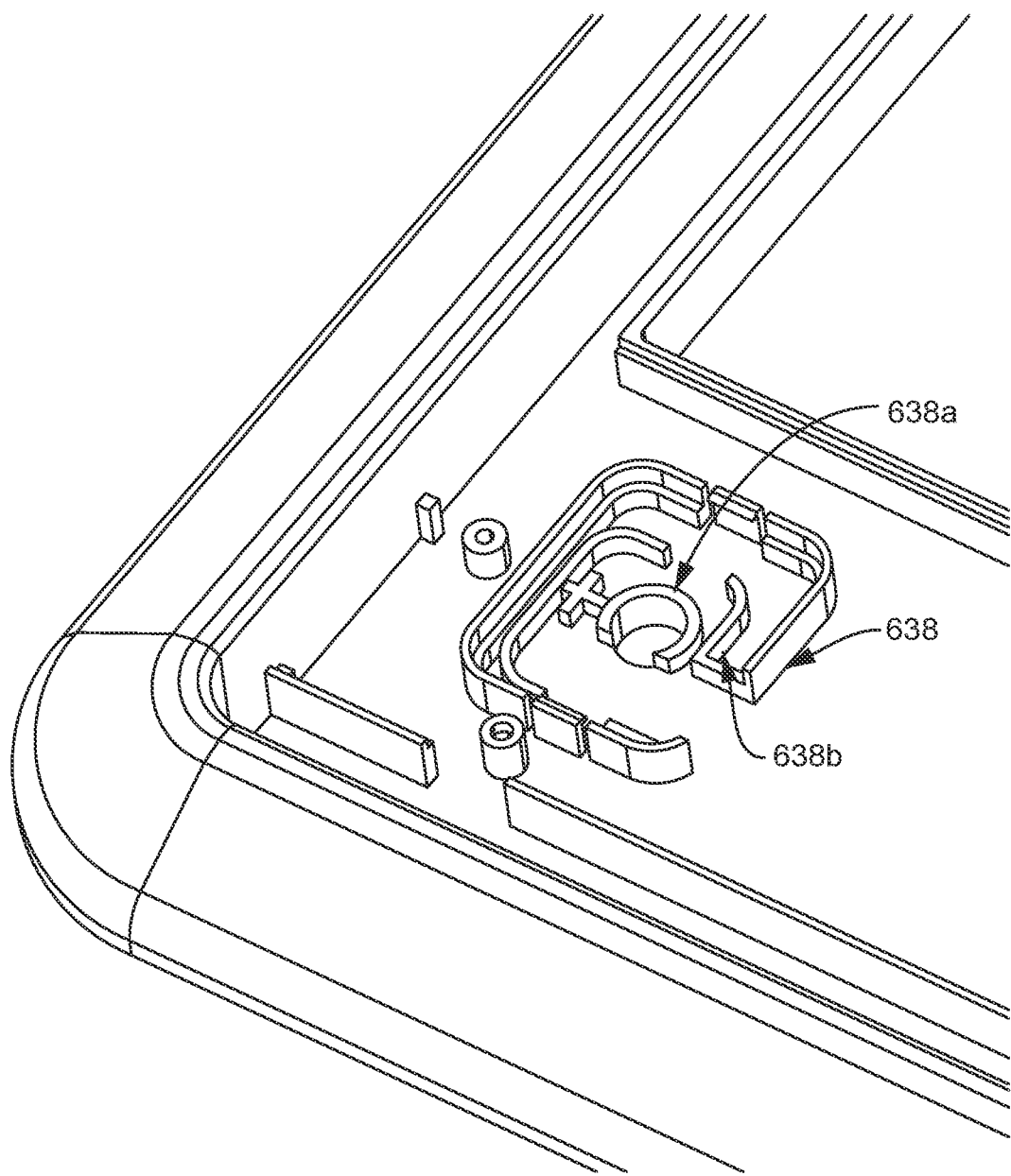
FIG. 15 depicts an enlarged view of a portion of a bottom housing of the scale device depicted in FIG. 10.

The sensors 632 can be disposed between the pads 636 and bottom portion of the housing 630. The sensors 632 can be seated in a receptacle 638 having a bottoming out feature 638a, as depicted in FIG. 15. The receptacle 638 can be coupled to or integrally formed with the bottom portion of the housing 630. The receptacle 638 can be configured to protect and/or support the sensor 632. The bottoming out feature 638a of the receptacle 638 can be configured to prevent the sensor 632 from bottoming out beyond a predefined extent, e.g., when too much force (e.g., force above a predefined threshold) is being exerted on the surface of the panel 610. The receptacle 638 can also include surrounding structure 638b that is raised relative to the bottoming out feature 638a to provide support to the sensor 632 along an outer portion of the sensor 632.

The scale assembly 600 differs from the scale assembly 400 in that downward displacement of the panel 610 (e.g., when a user places his foot on the panel 610) causes a corresponding downward displacement of the sensors 632. In particular, when a user places his foot on the panel 610, the panel can depress or displace downwards, which causes the pads 636 and correspondingly the extensions 634 to displace downwards and push downwards on a central portion of the sensor 632. Such displacement of the sensor 632 can be captured as a signal that is sent to a processor (e.g., an onboard processor of the scale assembly 600), which can then process and/or analyze the signal, as described above. In contrast, in the scale assembly 400, described above, downward displacement of the panel 410 causes a corresponding upward displacement of the sensor 432. Nonetheless, in both scale assemblies 400, 600, the sensors 432, 632 can be configured to measure forces that are exerted on the panels 410, 420, 610, 620, and to provide signals representative of such forces to a processor for further processing and/or analysis.

Scale assembly 600 can be designed with less separable parts, e.g., housing 630, 640 that is integrated with a surround structure, panels 610, 620 that are fixed to the housing 630, 640, etc., such that easier assembly of scale assembly 600 can be achieved. Nonetheless, in some embodiments, certain components of scale assembly 600 can be removable to assist with cleaning and/or maintenance of various components of scale assembly 600.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The invention claimed is:

1. An apparatus, comprising:
   a scale configured to be disposed on a surface in front of a toilet, the scale including:
      a panel having a flat surface configured to receive a foot of a subject seated on the toilet; and
      a first set of force sensors disposed below the panel and distributed about a perimeter of the panel, the first set of force sensors configured to collectively measure forces present on the panel when the foot is received on the panel;
   a surround structure disposed around the perimeter of the scale, the surround structure including:
      a sloped portion configured to extend gradually from the surface to the flat surface of the panel; and
      a ledge configured to prevent tipping of the panel when forces are applied to a corner or an edge of the panel; and
   a processor configured to:
      receive first signals indicative of the forces measured by the first set of force sensors;
      determine, based on the first signals, a partial weight of the subject carried by the foot of the subject when the subject is seated;
      receive second signals from a second set of force sensors disposed about a ring of the toilet, the second signals indicative of forces present on the ring when the subject is seated on the ring; and determine a total weight of the subject based on the first and the second signals.

2. The apparatus of claim 1, wherein each of the first and second signals are independent signals representative of dynamic forces measured by the respective sensors of the first and the second set of force sensors, and the processor is further configured to determine a posture of the subject based on the first and second signals.

3. The apparatus of claim 1, wherein the scale further includes:

a set of bases, each base configured to contact the surface on which the scale is disposed; and a set of struts, each strut from the set of struts coupled to a sensor from the first set of force sensors and a base from the set of bases such that, when the foot is received on the panel, the panel can displace toward the set of bases and cause each strut to transfer a signal associated with the displacement of the panel to the sensor coupled to each strut, the first set of force sensors configured to collectively measure the forces present on the panel based on the signals transferred by the set of struts.

4. The apparatus of claim 1, wherein each sensor from the first set of force sensors is configured to provide an independent signal representative of the dynamic forces present on the panel when the foot is received on the panel, and the processor is further configured to:

receive the independent signals from the first set of force sensors;

reduce noise in one or more of the independent signals by comparing the independent signals to one another; and determine a partial weight of the subject carried by the foot of the subject when the subject is seated based on the independent signals after reducing the noise.

5. The apparatus of claim 1, wherein the scale and the surround structure define a convex shape configured to fit against and surround a front portion of a base of the toilet.

6. The apparatus of claim 1, wherein the surround structure is spaced from the panel during normal use to avoid interfering with the measurements of the first set of force sensors.

7. An apparatus, comprising:

a first and a second panel, each panel configured to receive a different foot of a subject seated on a toilet;

a first and a second housing configured to couple to one another, each of the first and second housings including a portion that supports and prevents lateral movement of the first or the second panel;

a set of sensors including a first subset of sensors disposed within the first housing and a second subset of sensors disposed within the second housing, the first and the second subset of sensors configured to measure forces present on the first and the second panels respectively received within the first and the second housing when the feet of the subject seated on the toilet are placed on the first and the second panels; and a set of pads including a pad disposed above each sensor of the set of sensors, the set of pads extending through openings defined in the first and the second housings and engaging with the first and the second panels respectively received within the first and the second housings, the set of pads configured to displace downwards in response to the forces being present on the first and the second panels to cause a downward displacement of the set of sensors that corresponds with the forces present on the first and the second panels.

8. The apparatus of claim 7, wherein the set of pads include extensions that contact and displace the set of sensors in response to the forces being present on the first and the second panels.

9. The apparatus of claim 7, further comprising:

a communication interface configured to send signals indicative of the measured forces to a processor such that the processor, in response to receiving the signals, determines a partial weight of the subject carried by the feet of the subject when the subject is seated based on the signals.

10. The apparatus of claim 7, further comprising:

a processor operatively coupled to the set of sensors, the processor being configured to determine a partial weight of the subject carried by the feet of the subject when the subject is seated based on the signals.

11. The apparatus of claim 10, wherein the set of sensors is a first set of force sensors and the signals are first signals, and the processor is further configured to receive second signals from a second set of force sensors disposed about a ring of the toilet, the second signals indicative of forces present on the ring when the subject is seated on the ring, the processor configured to determine a total weight of the subject based on the first and second signals.

12. The apparatus of claim 7, further comprising a first and a second impedance sensors disposed on the first and the second panels, the first and the second impedance sensors configured to measure a foot-to-foot impedance of the subject when the feet of the subject are placed on the first and the second panels.

13. The apparatus of claim 12, further comprising a processor that is operatively coupled to the first and second impedance sensors and to a set of impedance sensors disposed on a ring of the toilet, the processor configured to:

receive a signal representative of the foot-to-foot impedance of the subject from the first and second impedance sensors;

receive a signal representative of a butt cheek-to-butt cheek impedance of the subject from the set of impedance sensors disposed on the ring of the toilet; and determine an impedance of the legs of the subject based on the foot-to-foot impedance and the butt cheek-to-butt cheek impedance.

14. The apparatus of claim 7, wherein the first and the second housing collectively define an area shaped to mate with a front portion of a base of a toilet.

15. The apparatus of claim 7, wherein the first subset of sensors and the second subset of sensors are configured to measure the forces present on the first panel and the second panel independently.

16. A system, comprising:

a first set of sensors disposed about a ring of a toilet, the first set of sensors configured to collectively measure forces present on the ring when a subject is seated on the ring;

a scale assembly configured to be disposed adjacent to the toilet, the scale assembly including:

a first scale having a first panel configured to receive a foot of the subject;

a second scale having a second panel configured to receive another foot of the subject; and a second set of sensors including a first subset of sensors disposed beneath the first panel and a second subset of sensors disposed beneath the second panel, the second set of sensors configured to measure forces present on the first and the second panel when the feet are received on the first and the second panel, the first and the second scales being arranged adjacent to one another to receive the feet of the subject when the subject is seated on the ring; and the first and the second scales configured to measure forces present on the first panel and the second panel independently; and a processor operatively coupled to the first and the second sets of sensors and configured to receive signals indicative of the forces measured by the first and the second sets of sensors, the processor configured to determine at least one of a total weight, a partial weight, or a posture of the subject based on the signals.

17. The system of claim 16, wherein the processor is disposed in the scale assembly or the ring.

18. The system of claim 16, wherein the scale assembly further includes a surround structure disposed around the scale assembly and configured to reduce lateral displacement of one or more components of the scale assembly during use, the surround structure defining a convex shape configured to fit against a front portion of a base of the toilet.

19. The system of claim 16, wherein each sensor from the second set of sensors is configured to provide an independent signal representative of the dynamic forces present on the first and the second panel when the feet are received on the first and the second panel, wherein the processor is further configured to:

receive the independent signals from the second set of sensors;

reduce noise in one or more of the independent signals by comparing the independent signals to one another; and determine the total weight, the partial weight, or the posture of the subject based on the independent signals after reducing the noise.

20. The system of claim 16, further comprising a first and a second impedance sensors disposed on at least one of the first or the second panel, the first and the second impedance sensors configured to measure a foot-to-foot impedance of the subject when the feet of the subject are received on the first and the second panel.

21. The system of claim 20, further comprising a set of impedance sensors disposed on the ring of the toilet, the processor further configured to:

receive a signal representative of the foot-to-foot impedance of the subject from the first and second impedance sensors;

receive a signal representative of a butt cheek-to-butt cheek impedance of the subject from the set of impedance sensors disposed on the ring of the toilet; and determine an impedance of the legs of the subject based on the foot-to-foot impedance and the butt cheek-to-butt cheek impedance.

22. An apparatus, comprising:

a first scale configured to be disposed on a surface in front of a toilet, the first scale including:

a first panel having a flat surface configured to receive a foot of a subject seated on the toilet; and a first set of sensors disposed below the panel and distributed about a perimeter of the panel;

a second scale including a second set of sensors; the second scale arranged adjacent to the first scale such that the subject seated on the toilet can place the foot on the first panel of the first scale and another foot on a second panel of the second scale, the first and the second set of sensors configured to collectively measure forces present on the first and the second panel of the first and the second scale when the feet of the subject are placed on the first and the second panel; and a surround structure disposed around the perimeter of the first scale and the second scale, the surround structure including:

a sloped portion configured to extend gradually from the surface to the flat surface of the first and the second panel; and a ledge configured to prevent tipping of the first and the second panel when forces are applied to a corner or an edge of the first panel.

23. The apparatus of claim 22, wherein the first scale is spaced from the second scale by a section of the surround structure extending between the first and the second scales.

24. The apparatus of claim 22, further comprising a first and a second impedance sensors, the first and the second impedance sensors configured to measure a foot-to-foot impedance of the subject when the feet of the subject are placed on the first and the second panel.

25. The apparatus of claim 24, further comprising a processor that is operatively coupled to the first and the second impedance sensors and to a set of impedance sensors disposed on a ring of the toilet, the processor configured to:

receive a signal representative of the foot-to-foot impedance of the subject from the first and the second impedance sensors;

receive a signal representative of a butt cheek-to-butt cheek impedance of the subject from the set of impedance sensors disposed on the ring of the toilet; and determine an impedance of the legs of the subject based on the foot-to-foot impedance and the butt cheek-to-butt cheek impedance.

26. An apparatus, comprising:

a scale configured to be disposed on a surface in front of a toilet, the scale including:

a panel having a flat surface configured to receive a foot of a subject seated on the toilet; and a set of sensors disposed below the panel and distributed about a perimeter of the panel, the set of sensors configured to collectively measure forces present on the panel when the foot is received on the panel; and a surround structure disposed around the perimeter of the scale, the surround structure including:

a sloped portion configured to extend gradually from the surface to the flat surface of the panel; and a ledge configured to prevent tipping of the panel when forces are applied to a corner or an edge of the panel;

the scale and the surround structure defining a convex shape configured to fit against and surround a front portion of a base of the toilet.

27. The apparatus of claim 26, further comprising:

a communication interface configured to send signals indicative of the measured forces to a processor such that the processor, in response to receiving the signals, determines a partial weight of the subject carried by the foot of the subject when the subject is seated based on the signals.

28. The apparatus of claim 27, further comprising:

a processor operatively coupled to the set of sensors, the processor being configured to determine a partial weight of the subject carried by the foot of the subject when the subject is seated based on the signals.

29. An apparatus, comprising:

a first and a second panel, each panel configured to receive a different foot of a subject seated on a toilet;

a first and a second housing configured to couple to one another, each of the first and second housings including a portion that supports and prevents lateral movement of the first or the second panel;

a first set of sensors including a first subset of sensors disposed within the first housing and a second subset of sensors disposed within the second housing, the first and the second subset of sensors configured to measure forces present on the first and the second panels respectively received within the first and the second housing when the feet of the subject seated on the toilet are placed on the first and the second panels; and a processor operatively coupled to the first set of sensors and a second set of sensors disposed about a ring of the toilet, the processor being configured to:

receive first signals indicative of the forces measured by the first set of sensors;

determine a partial weight of the subject carried by the feet of the subject when the subject is seated;

receive second signals from the second set of sensors, the second signals indicative of forces present on the ring when the subject is seated on the ring; and determine a total weight of the subject based on the first and the second signals.

30. The apparatus of claim 29, further comprising a first and a second impedance sensors disposed on the first and the second panels, the first and the second impedance sensors configured to measure a foot-to-foot impedance of the subject when the feet of the subject are placed on the first and the second panels.

31. The apparatus of claim 29, wherein the first and the second housing collectively define an area shaped to mate with a front portion of a base of a toilet.

32. The apparatus of claim 29, wherein the first subset of sensors and the second subset of sensors are configured to measure the forces present on the first panel and the second panel independently.

* * * * *